United States Patent
Medina-Kauwe

(10) Patent No.: US 10,752,893 B2
(45) Date of Patent: *Aug. 25, 2020

(54) ISOLATING TRAFFIC-ENHANCING MUTANTS OF DRUG DELIVERY PROTEIN

(71) Applicant: CEDARS-SINAI MEDICAL CENTER, Los Angeles, CA (US)

(72) Inventor: Lali K. Medina-Kauwe, Porter Ranch, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/017,866

(22) Filed: Jun. 25, 2018

(65) Prior Publication Data

US 2018/0298376 A1   Oct. 18, 2018

Related U.S. Application Data

(63) Continuation of application No. 14/419,233, filed as application No. PCT/US2013/053493 on Aug. 2, 2013, now Pat. No. 10,036,009.

(60) Provisional application No. 61/679,306, filed on Aug. 3, 2012.

(51) Int. Cl.

| A61K 38/00 | (2006.01) |
| A61P 35/00 | (2006.01) |
| C40B 10/00 | (2006.01) |
| C07K 1/00 | (2006.01) |
| C07K 14/00 | (2006.01) |
| C07K 17/00 | (2006.01) |
| C12N 15/10 | (2006.01) |
| C12N 15/87 | (2006.01) |
| C07K 14/005 | (2006.01) |
| A61K 47/64 | (2017.01) |

(52) U.S. Cl.
CPC ........ *C12N 15/1058* (2013.01); *A61K 47/645* (2017.08); *C07K 14/005* (2013.01); *C12N 15/1037* (2013.01); *C12N 15/87* (2013.01); *C12N 2710/10322* (2013.01); *C12N 2710/10341* (2013.01)

(58) Field of Classification Search
None
See application file for complete search history.

(56) References Cited

U.S. PATENT DOCUMENTS

| 5,439,829 A | 8/1995 | Anderson et al. |
| 5,547,945 A | 8/1996 | Ye et al. |
| 5,559,099 A | 9/1996 | Wickham et al. |
| 5,885,808 A | 3/1999 | Spooner et al. |
| 6,084,083 A | 7/2000 | Levinson et al. |
| 6,270,747 B1 | 8/2001 | Nadel et al. |
| 6,287,792 B1 | 9/2001 | Pardridqe et al. |
| 6,333,396 B1 | 12/2001 | Filpula et al. |
| 6,339,070 B1 | 1/2002 | Emery et al. |
| 9,078,927 B2* | 7/2015 | Medina-Kauwe ............ A61K 49/0056 |
| 9,789,201 B2* | 10/2017 | Medina-Kauwe ............ A61K 49/0056 |
| 9,850,293 B2* | 12/2017 | Medina-Kauwe ... A61K 31/713 |
| 10,036,009 B2* | 7/2018 | Medina-Kauwe ..... C12N 15/87 |
| 10,183,078 B2* | 1/2019 | Medina-Kauwe ... A61K 9/0019 |
| 2001/0055783 A1 | 12/2001 | Allnutt et al. |
| 2003/0138432 A1 | 7/2003 | Glazier |
| 2003/0170826 A1 | 9/2003 | Rabinovich et al. |
| 2005/0042753 A1 | 2/2005 | Yang et al. |
| 2005/0048606 A1 | 3/2005 | Wang et al. |
| 2005/0277193 A1 | 12/2005 | Wickham et al. |
| 2006/0014712 A1 | 1/2006 | Neuman |
| 2006/0093674 A1 | 5/2006 | Slobodkin et al. |
| 2008/0234183 A1 | 9/2008 | Hallbrink et al. |
| 2009/0009441 A1 | 1/2009 | Yamamoto et al. |
| 2011/0052697 A1 | 3/2011 | Farokhzad et al. |
| 2012/0004181 A1* | 1/2012 | Medina-Kauwe ... C07K 14/005 514/19.3 |
| 2015/0240231 A1 | 8/2015 | Medina-Kauwe |
| 2016/0060316 A1 | 3/2016 | Medina-Kauwe et al. |
| 2016/0331840 A1 | 11/2016 | Medina-Kauwe |
| 2018/0028678 A1* | 2/2018 | Medina-Kauwe ............ A61K 49/0056 |
| 2018/0066033 A1* | 3/2018 | Medina-Kauwe ... A61K 31/713 |

(Continued)

FOREIGN PATENT DOCUMENTS

| EP | 1 266 963 A1 | 12/2002 |
| JP | H10-505242 A | 5/1998 |
| JP | H11-501219 A | 2/1999 |

(Continued)

OTHER PUBLICATIONS

Shayakhmetov et al. "Deletion of Penton RGD Motifs Affects the Efficacy of both the Internalization and the Endosome Escape of Viral Particles Containing Adenovirus Serotype 5 or 35 Fiber Knobs" J. Virol. 79:1053-1061. (Year: 2005).*

(Continued)

*Primary Examiner* — Larry D Riggs, II
*Assistant Examiner* — Zachary J Miknis
(74) *Attorney, Agent, or Firm* — Morrison Foerster LLP

(57) ABSTRACT

The invention relates to methods for isolating traffic-enhancing mutants of drug delivery proteins. In one embodiment, the invention provides a carrier for delivering a therapeutic agent to an organelle, comprising a polypeptide encoded by a mutant penton base gene. In another embodiment, the invention provides a method of enhancing trafficking to a cell by administering a composition comprising a penton base (PB) protein with one or more mutations that enhance cellular entry.

20 Claims, 16 Drawing Sheets
Specification includes a Sequence Listing.

(56) References Cited

U.S. PATENT DOCUMENTS

| | | | | |
|---|---|---|---|---|
| 2019/0142962 A1* | 5/2019 | Medina-Kauwe | ... | A61K 9/0019 424/184.1 |
| 2019/0175747 A1* | 6/2019 | Medina-Kauwe | ... | A61K 31/704 |

FOREIGN PATENT DOCUMENTS

| | | | | |
|---|---|---|---|---|
| JP | 2001-521376 A | 11/2001 | | |
| RU | 2119341 C1 | 9/1998 | | |
| WO | WO-1996/07734 A2 | 3/1996 | | |
| WO | WO-1997/20051 A2 | 6/1997 | | |
| WO | WO-1998/35036 A1 | 8/1998 | | |
| WO | WO-2002/24934 A1 | 3/2002 | | |
| WO | WO-2009/009441 A2 | 1/2009 | | |
| WO | WO-2009009441 A2 * | 1/2009 | ......... | A61K 49/0056 |
| WO | WO-2009073104 A2 * | 6/2009 | ........... | C07K 14/005 |
| WO | WO-2010/085665 A2 | 7/2010 | | |
| WO | WO-2010/085665 A3 | 7/2010 | | |
| WO | WO-2013/052859 A2 | 4/2013 | | |
| WO | WO-2013/052859 A3 | 4/2013 | | |
| WO | WO-2014/182868 A1 | 11/2014 | | |
| WO | WO-2015/109264 A1 | 7/2015 | | |
| WO | WO-2015/154059 A2 | 10/2015 | | |
| WO | WO-2015/154059 A3 | 10/2015 | | |

OTHER PUBLICATIONS

Pakula, A.A. et al. (1989). "Genetic Analysis of Protein Stability and Function," Annu. Rev. Genet. 23:289-310.

Agadjanian, H. et al. (Feb. 2006). "Specific Delivery of Corroles to Cells via Noncovalent Conjugates with Viral Proteins," *Pharmaceutical Research* 23(2):367-377.

Agadjanian, H. et al. (Apr. 14-18, 2007). "Modified Viral Capsid Protein Mediates Non-Viral Targeting of Unique Non-Covalent Drug Conjugates to HER2+ Breast Cancer Cells," *Proceedings of the AACR Annual Meeting* 48:357, Abstract # 1505, 2 pages. (Abstract Only).

Agadjanian, H. et al. (Apr. 14, 2009). "Tumor Detection and Elimination by a Targeted Gallium Corrole," *Proc. Natl. Acad. Sci. USA* 106(15):6105-6110.

Agadjanian, H. et al. (Mar. 2012). "Chemotherapy Targeting by DNA Capture in Viral Protein Particles," *Nanomedicine* 7(3):335-352.

Aguilar, Z. et al. (1999). "Biologic Effects of Heregulin/neu Differentiation Factor on Normal and Malignant Human Breast and Ovarian Epithelial Cells," *Oncogene* 18:6050-6062.

Baselga, J. et al. (Mar. 1996). "Phase II Study of Weekly Intravenous Recombinant Humanized Anti-p185$^{HER2}$ Monoclonal Antibody in Patients with HER2/neu-Overexpressing Metastatic Breast Cancer," *J. Clin. Oncol.* 14(3):737-744.

Cherry, J.R. et al. (Apr. 1999). "Directed Evolution of a Fungal Peroxidase," *Nature Biotechnology*, 17(4):379-384, (Apr. 1999).

Faltus, T. et al. (Nov./Dec. 2004). "Silencing of the HER2/neu Gene by siRNA Inhibits Proliferation and Induces Apoptosis in HER2/neu-Overexpressing Breast Cancer Cells," *Neoplasia* 6(6):786-795.

Frankel, A.E. et al. (Feb. 2000). "Targeted Toxins," *Clin. Cancer Res.*, 6:326-334.

Genbank (Mar. 19, 2012). "Titi Monkey Adenovirus ECC-2011 Penton Base Protein," NCBI Accession No. = AEK98451.

Goldman, R. et al. (1990). "Heterodimerization of the erbB-1 and erbB-2 Receptors in Human Breast Carcinoma Cells: A Mechanism for Receptor Transregulation," *Biochemistry* 29(50):11024-11028.

Hong, S.S. et al. (1999). "Cellular Uptake and Nuclear Delivery of Recombinant Adenovirus Penton Base," *Virology* 2662:163-177.

Jeschke, M. et al. (1995), "Targeted Inhibition of Tumor-Cell Growth by Recombinant Heregulin-Toxin Fusion Proteins," *International Journal of Cancer* 60(5):730-739.

Karayan et al: (Nov. 1997). "Structural and Functional Determinants in Adenovirus Type 2 Penton Base Recombinant Protein," *Journal of Virology* 71(11):8678-8689.

Krumpe Lauren R. H. et al. (Aug. 2006). "T7 lytic phage-displayed peptide libraries exhibit less sequence bias than M13 filamentous phage-displayed peptide libraries.", *Proteomics* 6(15):4210-4222.

Kute, T. et al. (2004), "Development of Herceptin Resistance in Breast Cancer Cells," *Cytometry Part A* 57:86-93.

Kwon et al. (Mar. 2008). "Designer Gene Delivery Vectors: Molecular Engineering and Evolution of Adeno-Associated Viral Vectors for Enhanced Gene Transfer," *Pharmaceutical Research*, 25(3):489-499.

Lewis, G.D. et al. (Mar. 15, 1996). "Growth Regulation of Human Breast and Ovarian Tumor Cells by Heregulin: Evidence for the Requirement of ErbB2 as a Critical Component in Mediating Heregulin Responsiveness," *Cancer Research* 56:1457-1465.

Maheshri N. et al. (Jan. 2006)."Directed evolution of adeno-associated virus yields enhanced gene delivery vectors", *Nature Biotechnology, Nature Publishing Group, US*, 24(2):198-204.

Medina-Kauwe, L.K.et al. (Aug. 24-29, 1997). "A Novel Gene Delivery System for Cell-Specific Targeting," FASEB Journal, 11(9):A863, Meeting: 17$^{th}$ International Congress of Biochemistry and Molecular Biology in conjunction with the Annual Meeting of the American Society for Biochemistry and Molecular Biology, San Francisco, CA, 1 page, (Abstract Only).

Medina-Kauwe, L.K. et al. (Sep. 2000). "Assessing the Binding and Endocytosis Activity of Cellular Receptors Using GFP-Ligand Fusions," *Bio Techniques* 29(3):602-609.

Medina-Kauwe, L.K. et al. (2001). "3PO, a Novel Nonviral Gene Delivery System Using Engineered Ad5 Penton Proteins," *Gene Therapy* 8(10):795-803.

Medina-Kauwe, L.K. et al. (2001). "Nonviral Gene Delivery to Human Breast Cancer Cells by Targeted Ad5 Penton Proteins," *Gene Therapy*, 8(23):1753-1761.

Medina-Kauwe, L.K. (Aug. 2002). "A Novel Gene Delivery System Targeted to Breast Cancer," Report by University of Southern California, Report Sponsored by U.S. Army Medical Research and Material Command, Fort Detrick, Maryland, 14 pages.

Medina-Kauwe, L.K. et al. (2002). "Using GFP-Ligand Fusions to Measure Receptor-Mediated Endocytosis in Living Cells," *Vitamins and Hormones*, 65:81-95.

Medina-Kauwe, L.K. et al. (Nov. 2002). Ad5 Capsid Protein Uptake and Trafficking in HeLa Cells. *Molecular Biology of the Cell*, 13(Supplement):541a-542a. Meeting: 42$^{nd}$ Annual Meeting of the American Society for Cell Biology. San Francisco, CA, USA. American Society for Cell Biology.

Medina-Kauwe, L.K. (Nov. 14, 2003). "Endocytosis of Adenovirus and Adenovirus Capsid Proteins," *Adv. Drug Delivery Rev.* 55(11):1485-1496.

Medina-Kauwe, L.K. (2003). "Heregulin-Targeted Protein Uptake for Breast Cancer," retrieved from <http://grantome.com/grant/NIH/R01-CA102126-01> last visited Jul. 14, 2017, 4 pages (Abstract Only).

Medina-Kauwe, L.K. (2004). "Heregulin-Targeted Protein Uptake for Breast Cancer," retrieved from <http://grantome.com/grant/NIH/R01-CA102126-02>, last visited Jul. 14, 2017, (Abstract Only).

Medina-Kauwe, L.K. (2005). "Heregulin-Targeted Protein Uptake for Breast Cancer," retrieved from <http://grantome.com/grant/NIH/R01-CA102126-03>, last visited Jul. 14, 2017, 4 pages (Abstract Only).

Medina-Kauwe, L.K. (2005). "Introduction to the Special Issue: Traveling the Intracellular Highway to Gene Therapy," *Gene Therapy* 12:863-864.

Medina-Kauwe, L.K. et al. (2005, e-pub. Aug. 4, 2005). "Intracellular Trafficking of Nonviral Vectors," *Gene Therapy*, 12(24):1734-1751.

Medina-Kauwe, L.K. (2006). "Heregulin-Targeted Protein Uptake for Breast Cancer," retrieved from <http://grantome.com/grant/NIH/R01-CA102126-04>, last visited Jul. 14, 2017, 4 pages, (Abstract Only).

Medina-Kauwe, L.K. (2006). "Non-Viral Mediated Gene Delivery for Therapeutic Applications," *Gene Therapy for Neurological Disorders*, (Chapter 8), pp. 115-140.

Medina-Kauwe, L.K. (2007). "A Novel Targeted Therapeutic Using Viral Capsid Protein," <http://grantome.com/grant/1R21CA116014-01A2>, last visited Jul. 14, 2017, 4 pages, (Abstract Only).

(56) References Cited

OTHER PUBLICATIONS

Medina-Kauwe (Jun. 2007). "Targeting siRNA Missiles to HER2+ Breast Cancer," retrieved from <http://www.dtic.mil/cgi-bin/GetTRDoc?AD=ADA472023> (13 pages).
Medina-Kauwe, L.K. (2008). "A Novel Targeted Therapeutic Using Viral Capsid Protein," <http://grantome.com/grant/R21CA116014-02>, last visited Jul. 14, 2017, 4 pages, (Abstract Only).
Medina-Kauwe (2008). "Targeting Sirna Missiles to Her2+ Breast Cancer", *U.S. Army Medical Research and Material Command Fort Detrick, Maryland*, (10 pages).
Medina-Kauwe, L.K. (2009). "Protein-DNA Drug Carriers for Tumor Targeting," retrieved from <http://grantome.com/grant/NIH/R01-CA129822-01A2>, last visited, Jul. 12, 2017, 5 pages, (Abstract Only).
Medina-Kauwe (Jun. 2009). "Targeting SiRNA Missiles to HER2+ Breast Cancer", *U.S. Army Medical Research and Material Command Fort Detrick, Maryland*, pp. 1-11.
Medina-Kauwe, L.K. (2010). "Tumor Targeted Corroles for Detection and Intervention," retrieved from<http://grantome.com/grant/NIH/R01-CA140995-01A1>, lasted visited Jul. 12, 2017, 5 pages, (Abstract Only).
Medina-Kauwe, L.K. (2010). "Protein-DNA Drug Carriers for Tumor Targeting," retrieved from <http://grantome.com/grant/NIH/R01-CA129822-02>, last visited, Jul. 14, 2017, 5 pages, (Abstract Only).
Medina-Kauwe, L.K. (2011). "Protein-DNA Drug Carriers for Tumor Targeting," retrieved from <http://grantome.com/grant/NIH/R01-CA129822-03>, last visited, Jul. 14, 2017, 5 pages, (Abstract Only).
Medina-Kauwe, L.K. (2011). "Tumor Targeted Corroles for Detection and Intervention," retrieved from <http://grantome.com/grant/NIH/R01-CA140995-02>, lasted visited Jul. 14, 2017, 5 pages, (Abstract Only).
Medina-Kauwe, L.K. (2012). "Protein-DNA Drug Carriers for Tumor Targeting," retrieved from <http://grantome.com/grant/NIH/R01-CA129822-04>, last visited Jul. 14, 2017, 5 pages, (Abstract Only).
Medina-Kauwe, L.K. (2012). "Tumor Targeted Corroles for Detection and Intervention," retrieved from <http://grantome.com/grant/NIH/R01-CA140995-03>, lasted visited Jul. 14, 2017, 5 pages, (Abstract Only).
Medina-Kauwe, L.K. (2013). "Tumor Targeted Corroles for Detection and Intervention," retrieved from <http://grantome.com/grant/NIH/R01-CA140995-04> lasted visited Jul. 14, 2017, 5 pages, (Abstract Only).
Medina-Kauwe, L.K. (Feb. 2013). "Development of Adenovirus Capsid Proteins for Targeted Therapeutic Delivery," *Ther. Deliv.* 4(2):267-277.
Medina-Kauwe, L.K. (2014). "Tumor Targeted Corroles for Detection and Intervention," retrieved from <http://grantome.com/grant/NIH/R01-CA140995-05>, lasted visited Jul. 14, 2017, 5 pages, (Abstract Only).
"Novagen, T7 Select System Manual", *Internet Citation*, (Jun. 2000), pp. 1-21.
Rentsendorj, A. (2006, epub. Feb. 16, 2008). "Typical and Typical Trafficking Pathways of Ad5 Penton Base Recombinant Protein: Implications for Gene Transfer," *Gene Therapy* 13:821-836.
Rentsendorj, A. et al. (May 2008) "Targeting siRNA Molecular Missiles to HER2+ Cancer Cells," *Experimental and Molecular Therapeutics* AACR Annual Meeting (Apr. 12-16, 2008), 4 pages, (Abstract Only).
Rentsendorj A. et al. (Oct. 14, 2014). "The Ad5 fiber Mediates Nonviral Gene Transfer in the Absence of the Whole Virus, Utilizing A Novel Cell Entry Pathway," *Gene Therapy*, Nature Publishing Group, GB, 12:225-237.
Schmidt, M. et al. (1999). "A Suppression of Metastasis Formation by Recombinant Single Chain Antibody-Toxin Targeted to Full-Length and Oncogenic Variant EGF Receptors," *Oncogene* 18:1711-1721.
Sepp-Lorenzino, L. et al. (Apr. 18, 1996). "Signal Transduction Pathways Induced by Heregulin in MDA-MB-453 Breast Cancer Cells," *Oncogene* 12(8):1679-1687.
Shafikhani, S. et al. (Aug. 1997). "Generation of Large Libraries of Random Mutants in Bacillus subtilis by PCR-Based Plasmid Multimerization," *BioTechniques* 23(2):304-310.
Sims et al. (Feb. 1, 2013). "Treating Trastuzumab-Resistant HER2+ Breast Cancers with a HER3-Targeted Nanoparticle," *Cancer Research*, 73(3 Supp.) Abstract No. A101. Meeting: AACR Special Conference on Tumor Invasion and Metastasis 2013. San Diego, CA, United States. Jan. 20, 2013-Jan. 23, 2013, 2 pages, (Abstract Only).
Sliwkowski et al. (May 20, 1994). "Coexpression of erbB2 and erbB3 proteins Reconstitutes a High Affinity Receptor for Heregulin," *Journal of Biological Chemistry*, 269(20):14661-14665.
Wan, L. et al. (Oct. 1998). "In vitro evolution of Horse Heart Myoglobin to Increase Peroxidase Activity," *Proc. Natl. Acad. Sci. USA*, 95:12825-12831.
Weinstein, E.J. et al. (1998). "The Oncogene Heregulin Induces Apoptosis in Breast Epithelial Cells and Tumors," *Oncogene* 17:2107-2113.
Wickman T.J. et al. (Dec. 1, 1995). "Targeting of Adenovirus Penton Base to New Receptors Through Replacement of its RGD Motif with Other Receptor-Specific Peptide Motifs" *Gene Therapy*, Nature Publishing Group, GB, 2(10):750-756.
You, L. et al. (1994). "Directed Evolution of Subtilisin E in Bacillus subtilis to Enhance Total Activity in Aqueous Dimethylformamide," *Protein Engineering* 9(1):77-83.
Yuan, L. et al. (Sep. 2005). "Laboratory-Directed Protein Evolution," *Microbiology and Molecular Biology Reviews* 69(3):373-392.
Zabner, J.et al. (Aug. 11, 1995). "Cellular and Molecular Barriers to Gene Transfer by a Cationic Lipid," *Journal of Biological Chemistry*, 270(32):18997-19007.
Zhao, H. et al. (Mar. 1998). "Molecular Evolution by Staggered Extension Process (StEP) in vitro Recombination," 16:258-261.
U.S. Appl. No. 15/703,323, filed Sep. 13, 2017, for Medina-Kauwe et al. (Copy not submitted herewith pursuant to the waiver of 37 C.F.R. § 1.98(a)(2)(iii) issued by the Office on Sep. 21, 2004).
Ivanenkov, V.V. et al. (Jan. 11, 1999). "Uptake and Intercellular Fate of Phage Display Vectors in Mammalian Cells," Biochimica et Biophysica Acta 1448:450-462.
U.S. Appl. No. 16/510,517, filed Jun. 27, 2018, for Medina-Kauwe et al. (Copy not submitted herewith pursuant to the waiver of 37 C.F.R. § 1.98(a)(2)(iii) issued by the Office on Sep. 21, 2004).
Albinsson, B. et al. (Nov. 1999). "Adenovirus Type 41 Lacks on RGD αv-Integrin Binding Motif on the Penton Base and Undergoes Delayed Uptake in A549 Cells," Virus Res. 64(2):125-136.

\* cited by examiner

Figure 8

Nucleic Acid Sequence:

```
TTTTGTTTACTTTAAGAAGGAGATATACAT
ATG CGG GGT TCT CAT CAT CAT CAT CAT CAT GGT ATG GCT AGC ATG
ACT GGT GGA CAG CAA ATG GGT CGG GAT CTG TAC GAC GAT GAC GAT
AAG GAT CGA TGG          ATG CGG CGC GCG GCG ATG TAT GAG GAA
GGT CCT CCT CCC TCC TAC GAG AGT GTG GTG AGC GCG GCG CCA GTG
GCG GCG GCG CTG GGT TCT CCC TTC GAT GCT CCC CTG GAC CCG CCG
TTT GTG CCT CCG CGG TAC CTG CGG CCT ACC GGG GGG AGA AAC AGC
ATC CGT TAC TCT GAG TTG GCA CCC CTA TTC GAC ACC ACC CGT GTG
TAC CTG GTG GAC AAC AAG TCA ACG GAT GTG GCA TCC CTG AAC TAC
CAG AAC GAC CAC AGC AAC TTT CTG ACC ACG GTC ATT TAA AAC AAT
GAC TAC AGC CCG GGG GAG GCA AGC ACA CAG ACC ATC AAT CTT GAC
GAC CGG TCG CAC TGG GGC GGT GAC CTG AAA ACC ATC CTG CAT ACC
AAC ATG CCA AAT GTG AAC GAG TTC ATG TTT ACC AAT AAG TTT AAG
GCG CGG GTG ATG GTG TCG CGC TTG CCT ACT AAG GAC AAT CAG GTG
GAG CTG AAA TAC GAG TGG GTG GAG TTC ACG CTG CCC GAG GGC AAC
TAC TCC GAG ACC ATG ACC ATA GAC CTT ATG AAC AAC GCG ATC GTG
GAG CAC TAC TTG AAA GTG GCC AGA CAG AAC GGG GTT CTG GAA AGC
GAC ATC GGG GTA AAG TTT GAC ACC CGC AAC TTC AGA CTG GGG TTT
GAN CAC GTC ACT GGT CTT GTC ATG CCT GGG GTA TAT ACA AAC GAA
GCC NNC CAT CCA GAC ATC ATT TTG CTG CCA GGA TGC GGG GTG GAC
TTC ACC CAC AGC CGC CTG AGC AAC TTG TTG GGC ATC CGC AAG CGG
CAA CCC TTN CAG GAN GGC TTT AGG ATC NNC NAC GAT GAT CTG GAG
GGT GGT ANC ATT CCC GCA CTG (SEQ ID NO: 1).
```

Capital and italicized bases indicate mutations from wildtype PB

Mutations

Base 397 (wt 289) C > T, Glutamine > Stop codon
Base 471 (wt 363) C > T, Glycine > Glycine

Predicted Amino Acid Sequence:

MRRAAMYEEGPPPSYESVVSAAPVAAALGSPFDAPLDPPFVPPRYLRPTGGRNSIRYS
ELAPLFDTTRVYLVDNKSTDVASLNYQNDHSNFLTTVI (SEQ ID NO: 2)

Number of amino acids: 96

Molecular weight: 10531.8

Theoretical pI: 5.15

Figure 9

Nucleic Acid Sequence:

TTTAAGAAGGAGANATACAT

```
ATG CGG GGT TCT CAT CAT CAT CAT CAT CAT GGT ATG GCT AGC ATG
ACT GGT GGA CAG CAA ATG GGT CGG GAT CTG TAC GAC GAT GAC GAT
AAG GAT CGA TGG GGA TCC ACG CGG CGC GCG GCG ATG TAT GAG GAA
GGT CCT CCT CCC TCC TAC GAG AGT GTG GTG AGC GCG GCG CCA GTG
GCG GCG GCG CTG GGT TCT CCC TTC GAT GCT CCC CTG GAC CCG CCG
TTT GTG CCT CCG CGG TAC CTG CGG CCT ACC GGG GGG AGA AAC AGC
ATC CGT TAC TCT GAG TGG GCA CCC CTA TTC GAC ACC ACC CGT GTG
TAC CTG GTG GAC AAC AAG TCA ACG GAT GTG GCA TCC CTG AAC TAC
CAG AAC GAC CAC AGC AAC TTT CTG ACC ACG GTC ATT CAA AAC AAT
GAC TAC AGC CCG GGG GAG GCA AGC ACA CAG ACC ATC AAT CTT GAC
GAC CGG TCG CAC TGG GGC GGC GAC CTG AAA ACC ATC CTG CAT ACC
AAC ATG CCA AAT GTG AAC GAG TTC ATG TTT ACC AAT AAG TTT AAG
GCG CGG GTG ATG GTG TCG CGC TTG CCT ACT AAG GAC AAT CAG GTG
GAG CTG AAA TAC GAG TGG GTG GAG TTC ACG CTG CCC GAG GGC AAC
TAC TCC GAG ACC ATG ACC ATA GAC CTT ATG AAC AAC GCG ATC GTG
GAG CAC TAC TTG AAA GTG GGC AGA CAG AAC GGG GTT CTG GAA AGC
GAC ATC GGG GTA AAG TTT GAC ACC CGC AAC TTC AGA CTG GGG TTT
GAC CCC GTC ACT GGT CTT GTC ATG CCT GGG GTA TAT ACA AAC GAA
GCC TTC CAT CCA GAC ATC ATT TTG CTG CCA GGA TGC GGG GTG GAC
TTC ACC CAC AGC CGC CTG ANC AAC TTG TTG GGC ATC CGC AAG CGG
CAN CCC TTC CAG GAG GNN TTT AGG ATC ANC NAC GAT GAT CNG GAG
GGN NGN ANN ATN CCC GCA CTG (SEQ ID NO: 3)
```

Capital and italicized bases indicate mutations from wildtype PB

Mutations
Base 110 (wt 2) T > C, Methionine > Threonine
Base 179 (wt 71) T > G, Leucine > Tryptophan
Base 1044 C > T, Serine > Serine
Base 1518 G > A, Valine > Valine

Predicted Amino Acid Sequence:

MRGSHHHHHHGMASMTGGQQMGRDLYDDDDKDRWGSTRRAAMYEEGPPPSYES
VVSAAPVAAALGSPFDAPLDPPFVPPRYLRPTGGRNSIRYSEWAPLFDTTRVYLVDN
KSTDVASLNYQNDHSNFLTTVIQNNDYSPGEASTQTINLDDRSHWGGDLKTILHTNM
PNVNEFMFTNKFKARVMVSRLPTKDNQVELKYEWVEFTLPEGNYSETMTIDLMNN
AIVEHYLKVGRQNGVLESDIGVKFDTRNFRLGFDPVTGLVMPGVYTNEAFHPDIILLP
GCGVDFTHSRLXNLLGIRKRXPFQEXFRIXXDDXEXXXXPAL (SEQ ID NO: 4)

Figure 10

Nucleic Acid Sequence:

TTTACTTTAAGAAGGAGANATACAT

```
ATG CGG GGT TCT CAT CAT CAT CAT CAT CAT GGT ATG GCT AGC ATG ACT GGT
GGA CAG CAA ATG GGT CGG GAT CTG TAC GAC GAT GAC GAT AAG GAT CGA TGG
       ATG CGG CGC GCG GCG ATG TAT GAG GAA GGT CCT CCT CCC TCC TAC
GAG AGT GCG GTG AGC GCG GCG CCA GTG GCG GCG GCG CTG GGT TCT CCC TTC
GAT GCT CCC CTG GAC CCG CCG TTT GTG CCT CCG CGG TAC CTG CGG CCT ACC
GGG GGG AGA AAC AGC ATC CGT TAC TCT GAG TTG GCA CCC CTA TTC GAC ACC
ACC CGT GTG TAC CTG GTG GAC AAC AAG TCA ACG GAT GTG GCA TCC CTG AAC
TAC CAG AAC GAC CAC AGC AAC TTT CTG ACC ACG GTC ATT TAA AAC AAT GAC
TAC AGC CCG GGG GAG GCA AGC ACA CAG ACC ATC AAT CTT GAC GAC CGG TCG
CAC TGG GGC GGC GAC CTG AAA ACC ATC CTG CAT ACC AAC ATG CCA AAT GTG
AAC GAG TTC ATG TTT ACC AAT AAG TTT AAG GCG CGG GTG ATG GTG TCG CGC
TTG CCT ACT AAG GAC AAT CAG GTG GAG CTG AAA TAC GAG TGG GTG GAG TTC
ACG CTG CCC GAG GGC AAC TAA TCC GAG ACC ATG ACC ATA GAC CTT ATG AAC
AAC GCG ATC GTG GAG CAC TAC TTG AAA GTG GGC AGA CAG AAC GGG GTT CTG
GAA AGC GAC ATC GGG GTA AAG TTT GAC ACC CGC AAC TTC AGA CTG GGG TTT
GAC CAC GTC ACT GGT CTT GTC ATG CCT GGG GTA TAT ACA AAC GAA GCC TTC
CAT CCA GAC ATC ATT TTG CTG CCA GGA TGC GGG GTG GAC TTC ACC CAC AGC
CGC CTG ANC AAC TTG NTG GGC ATC CGC AAG CGG CAA CCN TTN CAG GAG GGC
TTT AGG ATC ANC TAC GAT GAT CTG GAG GGT G (SEQ ID NO: 5)
```

Capital and italicized bases indicate mutations from wildtype

Mutations

Base 161 (wt 53) T > C, Valine > Alanine
Base 398 (wt 290) C > T, Glutamine > Stop
Base 633 (wt 525) C > A, Tyrosine > Stop
Base 780 (wt 672) C > A, Proline > Histidine

Amino Acid Sequence :

MRRAAMYEEGPPPSYESAVSAAPVAAALGSPFDAPLDPPFVPPRYLRPTGGRNSIRYSELAPL
FDTTRVYLVDNKSTDVASLNYQNDHSNFLTTVI (SEQ ID NO: 6)

Number of amino acids: 96

Molecular weight: 10503.7

Theoretical pI: 5.15

Figure 11

Nucleic Acid Sequence:

TTAAGAAGGAGANATACAT

```
ATG CGG GGT TCT CAT CAT CAT CAT CAT CAT GGT ATG GCT AGC ATG ACT GGT
GGA CAG CAA ATG GGT CGG GAT CTG TAC GAC GAT GAC GAT AAG GAT CGA TGG
ATG CGG CGC CCG GCG ATG TAT GAG GAA GGT CCT CCT CCC TAC TAC
GAG AGT GTC GTC AGC GCG GCG CCA GTG GCG GCG GCG CTG GGT TCT ACC TTC
GAT GCT CCC CTG GAC CCG CCG TTT GTG CCT CCG CGG TAC CTG CGG CCT ACC
GGG GGG AGA AAC AGC ATC CGT TAC TCT GAG TTG GCA CCC CTA TTC GAC ACC
ACC CGT GTC TAC CTG GTG GAC AAC AAG TCA ACG GAT GTG GCA TCC CTG AAC
TAC TAC AAC GAC CAC AGC AAC TTT CTG ACC ACG GTC ATT CAA AAC AAT GAC
TAC AGC CCG GGG GAG GCA AGC ACA CAG ACC ATC AAT CTT GAC GAC CGG TCG
CAC TGG GGC GGC GAC CTG AAA ACC ATC CTG CAT ACC AAC ATG CCA AAT GTG
AAC GAG TTC ATG TAT ACC AAT AAG TTT AAG GCG CGG GTG ATG GTG TCG CGC
TTG CCT ACT AAG GAC AAT CAG GTG GAG CTG AAA TAC GAG TGG GTG GGG TTC
ACG CTG CCC GAG GGC AAC TAC TCC GAG ACC ATG ACC ATA GAC CTT ATG AAC
AAC GCG ATC GTG GAG CAC TAC TTG AAA GTG GGC AGA CAG AAC GGG GTT CTG
GAA AGC GAC ATC GGG GTA AAG TTT GAC ACC CGC AAC TTC AGA CTG NGG TTT
GAC CCC GTC ACT GGT CTT GTC ATG CCT GGG GTA TAT ACA AAC GAA GCC TTC
CAT CCA GAC ATC ATT TTG CTG CCA GGA TGN GGG GTG GNC TTC ACC CAC AGC
CGC CNG AGC AAC TTG TTG GGC ATC CGC AAG CNG CAA CCN TTC TAG GAG GGC
TTT ANG ATC ACC TAC NAT GAT CTG GAG GGN (SEQ ID NO: 7)
```

Mutations

Base 149 (wt 41) C > A, Serine > Tyrosine
Base 199 (wt 91) C > A, Proline > Threonine
Base 361 (wt 253) C > T, Glutamine > Stop
Base 524 (wt 416) T > A Phenylalanine > Tyrosine
Base 608 (wt 500) A > G Glutamate > Glycine

Predicted Amino Acid Sequence:

MRRAAMYEEGPPPYYESVVSAAPVAAALGSTFDAPLDPPFVPPRYLRPTGGRNSIRYSELAPLFDTTR
VYLVDNKSTDVASLNY (SEQ ID NO: 8)

Number of amino acids: 84

Molecular weight: 9241.4

Theoretical pI: 5.17

Figure 12

Nucleic Acid Sequence:

TTTAAGAAGGAGANATACAT

```
ATG CGG GGT TCT CAT CAT CAT CAT CAT CAT GGT ATG GCT AGC ATG
ACT GGT GGA CAG CAA ATG GGT CGG GAT CTG TAC GAC GAT GAC GAT
AAG GAT CGA TGG        ATG CGC CGC GCG GCG ATG TAT GAG GAA
GGT CCT CCT CCC TCC TAC GAG AGT GTG GTG AGC GCG GCG CCA GTG
GCG GCG GCG CTG CGT TCT CCC TTC GAT GCT CCC CTG GAC CCG CCG
TTT GTG CCT CCG CGG TAC CTG CGG CCT ACC GGG GGG AGA AAC AGC
ATC CGT TAC TCT GAG TTG GCA CCC CTA TTC GAC ACC ACC CGT GTG
TAC CTG GTG GAC AAC AAG TCA ACG GAT GTG GCA TCC CTG AAC TAC
CAG AAC GAC CAC AGC AAC TTT CTG ACC ACG GTC ATT CAA AAC AAT
GAC TAC AGC CCG GGG GAG GCA AGC ACA CAG ACC ATC AAT CTT GAC
GAC CGG TCG CAC TGG GGC GGC GAC CTG AAA ACC ATC CTG CAT ACC
AAC ATG CCA AAT GTG AAC GAG TTC ATG TTT ACC AAT AAG TTT AAG
GCG CGG GTG ATG GTG TCG CGC TTG CCT ACT AAG GAC AAT CAG GTG
GAG CTG AAA TAC CAG TAC GTG GAG TTC ACG CTG CCC GAG GGC AAC
TAC TCC GAG ACC ATG ACC ATA GAC CTT ATG AAC AAC GCG ATC GTG
GAG CAC TAC TTG AAA GTG GGC AGA CAG AAC GGG GTT CTG GAA AGC
GAC ATC GGG GTA AAG TTT GAC ACC CGC AAC TTC AGA CTG GGG TTT
GAC CCC GTC ACT GGT CTT GTC ATG CCT GGG GTA TAT ACA AAC GAA
GCC TTC CAT CCA GAC ATC ATT TTG CTG CCA GGA TGC GGG GTG GNC
TTC ACC CAC AGC CGC CTG AGC AAC TTG TTG GGC ATC CNC AAG CNG
CAA CCC NTT CCA GGA GGG CTT TAG GAT CAC CTA CGA TGA TCT GGA
GGG (SEQ ID NO: 9)
```

Mutations

Base 602 (wt 494) G > A, Glutamine > Stop

Predicted Amino Acid Sequence:

MRRAAMYEEGPPPSYESVVSAAPVAAALGSPFDAPLDPPFVPPRYLRPTGGRNSIRYS
ELAPLFDTTRVYLVDNKSTDVASLNYQNDHSNFLTTVIQNNDYSPGEASTQTINLDD
RSHWGGDLKTILHTNMPNVNEFMFTNKFKARVMVSRLPTKDNQVELKYE (SEQ ID
NO: 10)

Number of amino acids: 164

Molecular weight: 18400.5

Theoretical pI: 5.58

Figure 13

Nucleic Acid Sequence:

TTTAAGAAGGAGANATACAT

```
ATG CGG GGT TCT CAT CAT CAT CAT CAT CAT GGT ATG GCT AGC ATG ACT GGT
GGA CAG CAA ATG GGT CGG GAT CTG TAC GAC GAT GAC GAT AAG GAT CGA TGG
         ATG CGG CGC GCG GCG ATG TAT GAG GAA GGT CCT CCT CCC TCC TAC
GAG AGT GTG GTG AGC GCG GCG CCA GTG GCG GCG GCG CTG GGT TCT CCC TTC
GAT GCT CCC CTG GAC CCG CCG TTT GTG CCT CCG CGA TAC CTG CGG CCT ACC
GGG GGG AGA AAC AGC ATC CGT TAC TCT GAG TTG GCA CCC CTA TTC GAC ACC
ACC CGT GTG TAC CTG GTG GAC TAC AAG TCA ACG GAT GTG GCA TCC CTG AAC
TAC CAG AAC GAC CAC AGC AAC TTT CTG ACC ACG GTC ATT CAA AAC AAT GAC
TAC AGC CCG GGG GAG GCA AGC ACA CAG ACC ATC AAT CTT GAC GAC CGG TCG
CAC TGG GGC GGC GAC CTG AAA ACC ATC CTG CAT ACC AAC ATG CCA AAT GTG
AAC GAG TTC ATG TTT ACC AAT AAG TTT AAG GCG CGG GTG ATG GTG TCG CGC
TTG CCT ACT AAG GAC AAT CAG GTG GAG CTG AAA TAC GAG TGG GTG GAG TTC
ACG ATG CCC GAG GGC AAC TAC TCC GAG ACC ATG ACC ATA GAC CTT ATG AAC
AAC GCG ATC GTG GAG CAC TAC TTG AAA GTG GGC AGA CAG AAC GGG GTT CTG
GAA AGC GAC ATC GGG GTA AAG TTT GAC ACC CGC AAC TTC AGA CTG GGG TTT
GAC CCC GTC ACT GGT CTT GTC ATG CCT GGG GTA TAT ACA AAC GAA GCC NTC
CAT CCA GAC ATC ATT TTG CTG CCA GGA TGC GGG GTG NAC TTC ACC CAC AGC
CGC CTG AGC AAC TTG TTG GGC ATC CGC AAG CGG CAA CCC NTN CCA GGA GGG
CTT TAG GNT CAC CTA CGA TGA TCT GGA GGG NTG GNA NCA TTC CCG CNC TGT
CTG CCA GGA TGC GGG GTG GAC TTC ACC CAC AGC CGC CTG AGC AAC TTG TTG
GGC ATC CGC AAG CGG CAA CCC TT CCA GGA GGG CTT TAG GAT CAC CTA C
```
(SEQ ID NO: 11)

Mutations

Base 285 (wt 178) A > G, Arg > Arg
Base 328 (wt 220) A > T, Asn > Tyr
Base 616 (wt 508) C > A, Leu > Met

Predicted Amino Acid Sequence:

MRRAAMYEEGPPPSYESVVSAAPVAAALGSPFDAPLDPPFVPPRYLRPTGGRNSIRYSELAPL
FDTTRVYLVDYKSTDVASLNYQNDHSNFLTTVIQNNDYSPGEASTQTINLDDRSHWGGDLK
TILHTNMPNVNEFMFTNKFKARVMVSRLPTKDNQVELKYEWVEFTMPEGNYSETMTIDLMN
NAIVEHYLKVGRQNGVLESDIGVKFDTRNFRLGFDPVTGLVMPGVYTNEAXHPDIILLPGCG
VXFTHSRLSNLLGIRKRQPXPGGL (SEQ ID NO: 12)

Number of amino acids: 271

Molecular weight: 30339.9

Theoretical pI: 5.70

Figure 14

Nucleic Acid Sequence:

TTTAAGAAGGAGANATACAT

```
ATG CGG GGT TCT CAT CAT CAT CAT CAT CAT GGT ATG GCT AGC ATG ACT GGT
GGA CAG CAA ATG GGT CGG GAT CTG TAC GAC GAT GAC GAT AAG GAT CGA TGG
          ATG CGG CGC GCC CCG ATG TAT GAG GAA GGT CCT CCT CCC TCC TAC
GAG AGT GTG GTG AGC GCG GCG CCA GTG GCG GCG GCG CTG GGT TCT CCC TTC
GAT GCT CCC CTG GAC CCG CCG TTT GTG CCT CCG CGG TAC CTG CGG CCT ACC
GGG GGG AGA AAC AGC ATC CGT TAC TCT CAG TTG GCA CCC CTA TTC GAC ACC
ACC CGT GTG TAC CTG GTG GAC AAC AAG TCA ACG GTG TGG CAT CCC TGA ACT
ACC AGA ACG ACC ACA GCA ACT TTC TGA CCA CGG TCA TTC AAA ACA GTG ACT
ACA GCC CGG GGG AGG CAA GCA CAC AGA CCA TCA ATC TTG ACG ACC GGT CGC
ACT GGG GCG GCG ACC TGA AAA CCA TCC TGC ATA CCA ACA TGC CAA ATG TGA
ACG AGT TCA TGT TTA CCA ATA AGT TTA AGG CGC GGG TGA TGG TGT CGC GCT
TGC CTA CTA AGG ACA ATC AGG TGG AGC TGA AAT ACG AGT GGG TGG AGT TCA
CGC TGC CCG AGG GCA ACT ACT CCG AGA CCA TGA CCA TAG ACC TTA TGA ACA
ACG CGA TCG TGG AGC ACT ACT TGA AAG TGG CGA GAC AGA ACG GGG TTC TGG
AAT GCG ACA TCG GGG TAA AGT TTG ACA CCC GCA ACT CAG ACT GGG GT TTG
ATC CCG TCA CTG GTC TTG TCA TGN CTG GGG TAT ATA CAA ACG AAG CCT TCC
ATC CAG ACA TCA TTT TGC TGC CAG GAT GCG GGG TGG ACT TCA CCC ACA GCC
GCC TGA GCA ACT TGN TGG GCA TCC GCA TGC GGC AAN CNT TNC NGG AGG GCT
TTA GGA TCA CCN ACG ATG ATC TGN AGG (SEQ ID NO: 13)
```

Mutations

Deletion at base 340 (wt 232) Causes a frame shift.
Wt amino acid sequence is:     ...Thr-Asp-Val-Ala-Ser-Leu...
Mutated sequence is:           ...Thr-Val-Trp-His-Pro-Stop

Predicted Amino Acid Sequence:

5'3' Frame 1
G S Met R R A A Met Y E E G P P P S Y E S V V S A A P V A A A L G S P F D A P L D P F F Y P P R Y L R P T G G R N S I R Y S E L A P L F D T I R V Y L V D N K S T V W H P Stop (SEQ ID NO: 14)

Encodes 81 amino acids

Figure 15

Nucleic Acid Sequence:

TTTACTTTAAGAAGGAGANATACAT

ATG CGG GGT TCT CAT CAT CAT CAT NAT CAT GGT ATG GCT AGC ATG ACT GGT
GGA CAG CAA ATG GGT CGG GAT CTG TAC GAC GAT GAC GAT AAG GAT CGA TGG
ATG CGG CGC GCG GCG ATG TAT GAG GAA GGT CCT CCT CCC TCC TAC
GAG AGT GTG GTG AGC GCG GCG CCA GTG GCG GCG GCG CTG GGT TCT CCC TTC
GAT GCT CCC CTG GAC CCG CCG TTT GTG CCT CCG CGG TAC CTG CGG CCT ACC
GGG GGG AGA AAC AGC ATC CGT TAC TCT GAG TTG GCA CCC CTA TTC GAC ACC
ACC CGT GTG TAC CTG GTG GAC AAC AAG TCA ACG GTG TGG CAT CCC TGA ACT
ACC AGA ACG ACC ACA GCA ACT TTC TGA CCA CGG TCA TTC AAA ACA GTG ACT
ACA GCC CGG GGG AGG CAA GCA CAC AGA CCA TCA ATC TTG ACG ACC GGT CGC
ACT GGG GCG GCG ACC TGA AAA CCA TCC TGC ATA CCA ACA TGC CAA ATG TGA
ACG AGT TCA TGT TTA CCA ATA AGT TTA AGG CGC GGG TGA TGG TGT CGC GCT
TGC CTA CTA AGG ACA ATC AGG TGG AGC TGA AAT ACG AGT GGG TGG AGT TCA
CGC TGC CCG AGG GCA ACT ACT CCG AGA CCA TGA CCA TAG ACC TTA TGA ACA
ACG CGA TCG TGG AGC ACT ACT TGA AAG TGG GCA GAC AGA ACG GGG TTC TGG
AAT GCG ACA TCG GGG TAA AGT TTG ACA CCC GCA ACT TCA GAC TGG GGT TTG
ATC CCG TCA CTG GTC TTG TCA TGC CTG GGG TAT ATA CAA ACG AAG CCT TCC
ATC CAG ACA TCA TTT TGC TGC CAG GAT GCG GGG TGG ACT TCA CCC ACA GCC
GCC TGA GCA ACT TGT TGG GCA TCC GCA TGC GGC AAC CCT TNC AGG AGG GCT
TTA GGA TCA CCT ACG ATG ATC TGN AGG GNN GNA NCA TTN CCC GCA CTG NTG
GAN GT (SEQ ID NO: 15)
Deletion at base 340 (wt 232) Causes a frame shift.

Predicted Amino Acid Sequence:

MRRAAMYEEG PPPSYESVVS AAPVAAALGS PFDAPLDPPFVPPRYLRPTG
GRNSIRYSELAPLFDTTRVY LVDNKSTVWHP (SEQ ID NO: 16)

Number of amino acids: 81

Molecular weight: 8918.1

Theoretical pI: 6.54

Figure 16

Nucleic Acid Sequence:

ATTTTGTTTACTTTAAGAAGGAGATATACAT

ATG CGG GGT TCT CAT CAT CAT CAT CAT CAT GGT ATG GCT AGC ATG ACT GGT
GGA CAG CAA ATG GGT CGG GAT CTG TAC GAC GAT GAC GAT AAG GAT CGA TGG
CCG ATG CGG CGC GCG GCG ATG TAT GAG GAA GGT CCT CCT CCC TCC TAC
GAG AGT GTG GTG AGC GCG GCG CCA GTG GCG GCG GCG CTG GGT TCT CCC TTC
GAT GCT CCC CTG GAC CCG CCG TTT GTG CCT CCG CGG TAC CTG CGG CCT ACC
GGG GGG AGA AAC AGC ATC CGT TAC TCT GAG TTG GCA CCC CTA TTC GAC ACC
ACC CGT GTG TAC CTG GTG GAC AAC AAG TCA ACG GAT GTG GCA TCC CTG AAC
TAC CAG AAC GAC CAC AGC AAC TTT CTG ACC ACG GTC ATT CAA AAC AAT GAC
TAC AGC CCG GGG GAG GCA AGC ACA CAG ACC ATC AAT CTT GAC GAC CGG TCG
CAC TGG GGC GGC GAC CTG AAA ACC ATC CTG CAT ACC AAC ATG CCA AAT GTG
AAC GAG TTC ATG TTT ACC AAT AAG TTT AAG GCG CGG GTG ATG GTG TCG CGC
TTG CCT ACT AAG GAC AAT CAG GTG GAG CTG AAA TAC GAG TAC GTG GAG TTC
ACG CTG CCC GAG GGC AAC TAC TCC GAG ACC ATG ACC ATA GAC CTT ATG AAC
AAC GCG ATC GTG GAG CAC TAC TTG AAA GTG GGC AGA CAG AAC GGG GTT CTG
GAA AGC GAC ATC GGG GTA AAG TTT GAC ACC CGC AAC TTC AGA CTG GGG TTT
GAC CCC GTC ACT GGT CTT GTC ATG CCT GGG GTA TAT ACA AAC GAA GCC TNN
CAT CCA GAC ATC ATT TTG CTG CCA GGA TGC GGG GTG GAC TTC ACC CAC AGC
CGC CTG AGC AAC TTG TTG GGC ATC CNC AAG CGG CAA CCC TTN CAG G (SEQ
ID NO: 17)

Mutations

Base 602 (wt 494) G > A Glutamine > Stop. Same mutation as 331I

Predicted Amino Acid Sequence:

MRRAAMYEEGPPPSYESVVSAAPVAAALGSPFDAPLDPPFVPPRYLRPTGGRNSIRYSELAPL
FDTTRVYLVDNKSTDVASLNYQNDHSNFLTTVIQNNDYSPGEASTQTINLDDRSHWGGDLK
TILHTNMPNVNEFMFTNKFKARVMVSRLPTKDNQVELKYE (SEQ ID NO: 18)

Number of amino acids: 164

Molecular weight: 18400.5

Theoretical pI: 5.58

Figure 17

Nucleic Acid Sequence:

Pieced Together Sequence from the 5' and 3' Data by Bradley Reinfeld

```
ATG CGG GGT TCT CAT CAT CAT CAT CAT CAT GGT ATG GCT AGC ATG ACT GGT
GGA CAG CAA ATG GGT CGG GAT CTG TAC GAC GAT GAC GAT AAG GAT CGA TGG
ATG CGG CGC GCG GCG ATG TAT GAG GAA GGT CCT CCT CCC TCC TAC
GAG AGT GTG GTG AGC GCG GCG CCA GTG GCG GCG GCG CTG GGT TCT CCC TTC
GAT GCT CCC CTG GAC CCA CCG TTT GTG CCT CCG CGG TAC CTG CGG CCT ACC
GGG GGG AGA AAC AGC ATC CGT TAC TCT GAG TTG GCA CCC CTA TTC GAC ACC
ACC CGT GTG TAC CTG GTG GAC AAC AAG TCA ACG GAT GTG GCA TCC CTG AAC
TAC CAG AAC GAC CAC AGC AAC TTT CTG ACC ACG GTC ATT CAA AAC AAT GAC
TAC AGC CCG GGG GAG GCA AGC ACA CAG ACC ATC AAT CTT GAC GAC CGG TCG
CAC TGG GGC GGC GAC CTG AAA ACC ATC CTG CAT ACC AAC ATG CCA AAT GTG
AAC GAG TTC ATG TTT ACC AAT AAG TTT AAG GCG CGG GTG ATG GTG TCG CGC
TTG CCT ACT AAG GAC AAT CAG GTG GAG CTG AAA TAC GAG TGG GTG GAG TTN
ACG CTG CCC GAG GGC AAC TAC TCC GAG ACC ATG ACC ATA GAC CTT ATG AAC
AAC GCG ATC GTG GAG CAC TAC TTG AAA GTG GGC AGA CAG AAC GGG GTT CTG
GAA AGC GAC ATC GGG GTA AAG TTT GAC ACC CGC AAC TTC AGA CTG GGG TTT
GAC CCC GTC ACT GGT CTT GTC ATG CCT GGG GTA TAT ACA AAC GAA GCC TTC
CAT CCA GAC ATC ATT TTG CTG CCA GGA TGC GGG GTG GAC TTC ACC CAC AGC
CGC CTG AGC AAC TTG TTG GGC ATC CGC AAG CGG CAA CCC TTC CAG GAG GGC
TTT AGG ATC ACC TAC GAT GAT CTG GAG GGT GGT AAC ATT CCC GCA CTG TTC
GAT GTG GAC GCN TAC CAG GCG AGC TTG AAA GAT GAC ACC GAA CAG GGC GGC
GGT GGC GCA GGC GGC AGC AAC AGC AGT GGC AGC GGC GCG GAA GAG AAC TCC
AAC GCG GCA GCC GCG GCA ATG CAG CCG GTG GAG GAC ATG AAC GAT CAT GCC
ATT CGC GGC GAC ACC TTT GCC ACA CGG GCT GAG GAG AAG CGC GCT GAG GCC
GAA GCA GCG GCC GAA GCT GCC GCC CCC GCT GCG CAA CCC GAG GTC GAG AAG
CCT CAG GAG AAA CCG GTG ATC AAA CCC CTG ACA GAG GAC AGC AAG AAA CGC
AGT TAC AAC CTA ATA AGC AAT GAC AGC ACC TTC ACC CAG TAC CGC AGC TGG
TAC CTT GCA TAC AAC TAC GGC GAC CCT CAG ACC GGA ATC CGC TCA TGG ACC
CTG CTT TGC ACT CCT GAC GTA ACC TGC GGC TCG GAG CAG GTC TAC TGG TCG
TTG CCA GAC ATG ATG CAA GAC CCC ATG ACC TTC CGC TCC ACG CGC CAG ATC
AGC AAC TTT CCG GTG GTT GGC GCC GAG CTG TTG TCC GTG CAC TCC AAG AGC
TTC TAC AAC GAC CAG GCC GTC TAC TCC CAA CTC ATC CGC CAG TTT ACC TCT
CTG ACC CAC GTG TTC AAT CGC TTT CCC GAG AAC CAG ATT TTG GCG CGC CCG
CCA GCC CCC ACC ATC ACC ACC GTC AGT GAA AAC GTT CCT GCT CTC ACA GAT
CAC GGG ACG CTA CCG CTG CGC AAC AGC ATC GGA GGA GTC CAG CGA GTG ACC
ATT ACT GAC GCC AGA CGC CGC ACC TGC CCC TAC GTT TAC AAG GCC CTG GGC
ATA GTC TCG CCG CGC GTC CTA TCG AGC CGC ACT TTT TGA GAA TTC GAA GCT
TGA TCC GGC TGC TAA CAA AGC CCG AAA GGA AGC NGA GTN GGC TGC TGC CAC
C (SEQ ID NO: 19)
```

Figure 17 (continued)

Predicted Amino Acid Sequence:

MRRAAMYEEGPPPSYESVVSAAPVAAALGSPFDAPLDPPFVPPRYLRPTGGRNSIRYSEL
APLFDTTRVYLVDNKSTDVASLNYQNDHSNFLTTVIQNNDYSPGEASTQTINLDDRSHWGGD
LKTILHTNMPNVNEFMFTNKFKARVMVSRLPTKDNQVELKYEWVEXTLPEGNYSETMTIDL
MNNAIVEHYLKVGRQNGVLESDIGVKFDTRNFRLGFDPVTGLVMPGVYTNEAFHPDIHLLPG
CGVDFTHSRLSNLLGIRKRQPFQEGFRITYDDLEGGNIPAL░░░DXYQASLKDDTEQGGGGA
GGSNSSGSGAEENSNAAAAAMQPVEDMNDHAI░░░TFATRAEEKRAEAEAAAEAAAPAAQ
PEVEKPQEKPVIKPLTEDSKKRSYNLISNDSTFTQYRSWYLAYNYGDPQTGIRSWTLLCTPDV
TCGSEQVYWSLPDMMQDPMTFRSTRQISNFPVVGAELLSVHSKSFYNDQAVYSQLIRQFTSLT
HVFNRFPENQILARPPAPTITTVSENVPALTDHGTLPLRNSIGGVQRVTITDARRRTCPYVYKAL
GIVSPRVLSSRTF (SEQ ID NO: 20)

Number of amino acids: 571

Molecular weight: 63320.2

Theoretical pI: 5.25

SEQUENCE LISTING

```
<160> NUMBER OF SEQ ID NOS: 20

<210> SEQ ID NO 1
<211> LENGTH: 996
<212> TYPE: DNA
<213> ORGANISM: Homo sapiens
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (844)..(845)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (958)..(959)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t

<400> SEQUENCE: 1
ttttgtttac tttaagaagg agatatacat atgcggggtt ctcatcatca tcatcatcat      60
ggtatggcta gcatgactgg tggacagcaa atgggtcggg atctgtacga cgatgacgat     120
aaggatcgat ggggatccat gcggcgcgcg gcgatgtatg aggaaggtcc tcctccctcc     180
tacgagagtg tggtgagcgc ggcgccagtg gcggcggcgc tgggttctcc cttcgatgct     240
cccctggacc cgccgtttgt gcctccgcgg tacctgcggc ctaccggggg gagaaacagc     300
atccgttact ctgagttggc acccctattc gacaccaccc gtgtgtacct ggtggacaac     360
aagtcaacgg atgtggcatc cctgaactac cagaacgacc acagcaactt tctgaccacg     420
gtcatttaaa acaatgacta cagcccgggg gaggcaagca cacagaccat caatcttgac     480
gaccggtcgc actgggcgg tgacctgaaa accatcctgc ataccaacat gccaaatgtg     540
aacgagttca tgtttaccaa taagtttaag gcgcgggtga tggtgtcgcg cttgcctact     600
aaggacaatc aggtggagct gaaatacgag tgggtggagt tcacgctgcc cgagggcaac     660
tactccgaga ccatgaccat agaccttatg aacaacgcga tcgtggagca ctacttgaaa     720
gtgggcagac agaacggggt tctggaaagc gacatcgggg taaagtttga cacccgcaac     780
```

-continued

```
ttcagactgg ggtttganca cgtcactggt cttgtcatgc ctggggtata tacaaacgaa   840
gccnnccatc cagacatcat tttgctgcca ggatgcgggg tggacttcac ccacagccgc   900
ctgagcaact tgttgggcat ccgcaagcgg caaccctlnc agganggctt taggatcnnc   960
nacgatgatc tggagggtgg tancattccc gcactg                             996
```

```
<210> SEQ ID NO 2
<211> LENGTH: 96
<212> TYPE: PRT
<213> ORGANISM: Homo sapiens

<400> SEQUENCE: 2

Met Arg Arg Ala Ala Met Tyr Glu Glu Gly Pro Pro Ser Tyr Glu
1               5                   10                  15

Ser Val Val Ser Ala Ala Pro Val Ala Ala Leu Gly Ser Pro Phe
                20                  25                  30

Asp Ala Pro Leu Asp Pro Pro Phe Val Pro Pro Arg Tyr Leu Arg Pro
            35                  40                  45

Thr Gly Gly Arg Asn Ser Ile Arg Tyr Ser Glu Leu Ala Pro Leu Phe
        50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95
```

```
<210> SEQ ID NO 3
<211> LENGTH: 986
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (895)..(895)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (937)..(938)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (961)..(961)
<223> OTHER INFORMATION: n is a, c, g, or t
<220> FEATURE:
<221> NAME/KEY: misc_feature
<222> LOCATION: (968)..(969)
<223> OTHER INFORMATION: n is a, c, g, or t
<220> FEATURE:
<221> NAME/KEY: misc_feature
<222> LOCATION: (971)..(971)
<223> OTHER INFORMATION: n is a, c, g, or t
<220> FEATURE:
<221> NAME/KEY: misc_feature
<222> LOCATION: (973)..(974)
```

```
<223> OTHER INFORMATION: n is a, c, g, or t
<220> FEATURE:
<221> NAME/KEY: misc_feature
<222> LOCATION: (977)..(977)
<223> OTHER INFORMATION: n is a, c, g, or t

<400> SEQUENCE: 3
tttaagaagg aganatacat atgcggggtt ctcatcatca tcatcatcat ggtatggcta      60
gcatgactgg tggacagcaa atgggtcggg atctgtacga cgatgacgat aaggatcgat     120
ggggatccac gcggcgcgcg gcgatgtatg aggaaggtcc tcctccctcc tacgagagtg     180
tggtgagcgc ggcgccagtg gcggcggcgc tgggttctcc cttcgatgct ccctggacc      240
cgccgtttgt gcctccgcgg tacctgcggc ctaccggggg gagaaacagc atccgttact     300
ctgagtgggc acccctattc gacaccaccc gtgtgtacct ggtggacaac aagtcaacgg     360
atgtggcatc cctgaactac cagaacgacc acagcaactt tctgaccacg gtcattcaaa     420
acaatgacta cagcccgggg gaggcaagca cacagaccat caatcttgac gaccggtcgc     480
actgggcgg cgacctgaaa accatcctgc ataccaacat gccaaatgtg aacgagttca     540
tgtttaccaa taagtttaag gcgcgggtga tggtgtcgcg cttgcctact aaggacaatc     600
aggtggagct gaaatacgag tgggtggagt tcacgctgcc cgagggcaac tactccgaga     660
ccatgaccat agaccttatg aacaacgcga tcgtggagca ctacttgaaa gtgggcagac     720
agaacggggt tctggaaagc gacatcgggg taaagtttga cacccgcaac ttcagactgg     780
ggtttgaccc cgtcactggt cttgtcatgc ctggggtata tacaaacgaa gccttccatc     840
cagacatcat tttgctgcca ggatgcgggg tggacttcac ccacagccgc ctgancaact     900
tgttgggcat ccgcaagcgg canccttcc aggaggnntt taggatcanc nacgatgatc     960
nggagggnng nannatnccc gcactg                                          986

<210> SEQ ID NO 4
<211> LENGTH: 322
<212> TYPE: PRT
<213> ORGANISM: Homo sapiens
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (310)..(311)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (316)..(319)
<223> OTHER INFORMATION: Xaa can be any naturally occurring amino acid

<400> SEQUENCE: 4

Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
            20                  25                  30
```

Arg Trp Gly Ser Thr Arg Arg Ala Ala Met Tyr Glu Glu Gly Pro Pro
            35                  40                  45

Pro Ser Tyr Glu Ser Val Val Ser Ala Ala Pro Val Ala Ala Ala Leu
    50                  55                  60

Gly Ser Pro Phe Asp Ala Pro Leu Asp Pro Pro Phe Val Pro Pro Arg
65                  70                  75                  80

Tyr Leu Arg Pro Thr Gly Gly Arg Asn Ser Ile Arg Tyr Ser Glu Trp
                85                  90                  95

Ala Pro Leu Phe Asp Thr Thr Arg Val Tyr Leu Val Asp Asn Lys Ser
            100                 105                 110

Thr Asp Val Ala Ser Leu Asn Tyr Gln Asn Asp His Ser Asn Phe Leu
        115                 120                 125

Thr Thr Val Ile Gln Asn Asn Asp Tyr Ser Pro Gly Glu Ala Ser Thr
    130                 135                 140

Gln Thr Ile Asn Leu Asp Asp Arg Ser His Trp Gly Gly Asp Leu Lys
145                 150                 155                 160

Thr Ile Leu His Thr Asn Met Pro Asn Val Asn Glu Phe Met Phe Thr
                165                 170                 175

Asn Lys Phe Lys Ala Arg Val Met Val Ser Arg Leu Pro Thr Lys Asp
            180                 185                 190

Asn Gln Val Glu Leu Lys Tyr Glu Trp Val Glu Phe Thr Leu Pro Glu
        195                 200                 205

Gly Asn Tyr Ser Glu Thr Met Thr Ile Asp Leu Met Asn Asn Ala Ile
    210                 215                 220

Val Glu His Tyr Leu Lys Val Gly Arg Gln Asn Gly Val Leu Glu Ser
225                 230                 235                 240

Asp Ile Gly Val Lys Phe Asp Thr Arg Asn Phe Arg Leu Gly Phe Asp
                245                 250                 255

Pro Val Thr Gly Leu Val Met Pro Gly Val Tyr Thr Asn Glu Ala Phe
            260                 265                 270

His Pro Asp Ile Ile Leu Leu Pro Gly Cys Gly Val Asp Phe Thr His
        275                 280                 285

Ser Arg Leu Xaa Asn Leu Leu Gly Ile Arg Lys Arg Xaa Pro Phe Gln
    290                 295                 300

Glu Xaa Phe Arg Ile Xaa Xaa Asp Asp Xaa Glu Xaa Xaa Xaa Xaa Pro
305                 310                 315                 320

Ala Leu

```
<210> SEQ ID NO 5
<211> LENGTH: 974
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (908)..(908)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
```

<221> NAME/KEY: misc_feature
<222> LOCATION: (934)..(934)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t

<400> SEQUENCE: 5

```
tttactttaa gaaggagana tacatatgcg gggttctcat catcatcatc atcatggtat      60
ggctagcatg actggtggac agcaaatggg tcgggatctg tacgacgatg acgataagga     120
tcgatgggga tccatgcggc gcgcggcgat gtatgaggaa ggtcctcctc cctcctacga     180
gagtgcggtg agcgcggcgc cagtggcggc ggcgctgggt tctcccttcg atgctcccct     240
ggacccgccg tttgtgcctc cgcggtacct gcggcctacc gggggagaa acagcatccg      300
ttactctgag ttggcacccc tattcgacac cacccgtgtg tacctggtgg acaacaagtc     360
aacggatgtg gcatccctga actaccagaa cgaccacagc aactttctga ccacggtcat     420
ttaaaacaat gactacagcc cggggagggc aagcacacag accatcaatc ttgacgaccg     480
gtcgcactgg ggcggcgacc tgaaaaccat cctgcatacc aacatgccaa atgtgaacga     540
gttcatgttt accaataagt ttaaggcgcg ggtgatggtg tcgcgcttgc ctactaagga     600
caatcaggtg gagctgaaat acgagtgggt ggagttcacg ctgcccgagg caactaatc      660
cgagaccatg accatagacc ttatgaacaa cgcgatcgtg gagcactact tgaaagtggg     720
cagacagaac ggggttctgg aaagcgacat cggggtaaag tttgacaccc gcaacttcag     780
actggggttt gaccacgtca ctggtcttgt catgcctggg gtatatacaa acgaagcctt     840
ccatccagac atcattttgc tgccaggatg cggggtggac ttcacccaca gccgcctgan     900
caacttgntg ggcatccgca agcggcaacc nttncaggag ggctttagga tcanctacga     960
tgatctggag ggtg                                                       974
```

<210> SEQ ID NO 6
<211> LENGTH: 96
<212> TYPE: PRT
<213> ORGANISM: Homo sapiens

<400> SEQUENCE: 6

```
Met Arg Arg Ala Ala Met Tyr Glu Glu Gly Pro Pro Ser Tyr Glu
1               5                   10                  15

Ser Ala Val Ser Ala Ala Pro Val Ala Ala Leu Gly Ser Pro Phe
                20                  25                  30

Asp Ala Pro Leu Asp Pro Pro Phe Val Pro Arg Tyr Leu Arg Pro
                35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95
```

<210> SEQ ID NO 7
<211> LENGTH: 967
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (953)..(953)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t

<400> SEQUENCE: 7

| | | | | | |
|---|---|---|---|---|---|
| ttaagaagga | ganatacata | tgcggggttc | tcatcatcat | catcatcatg | gtatggctag   60 |
| catgactggt | ggacagcaaa | tgggtcggga | tctgtacgac | gatgacgata | aggatcgatg  120 |
| gggatccatg | cggcgcgcgg | cgatgtatga | ggaaggtcct | cctccctact | acgagagtgt  180 |
| ggtgagcgcg | gcgccagtgg | cggcggcgct | gggttctacc | ttcgatgctc | ccctggaccc  240 |
| gccgtttgtg | cctccgcggt | acctgcggcc | taccgggggg | agaaacagca | tccgttactc  300 |
| tgagttggca | cccctattcg | acaccacccg | tgtgtacctg | gtggacaaca | agtcaacgga  360 |
| tgtggcatcc | ctgaactact | agaacgacca | cagcaacttt | ctgaccacgg | tcattcaaaa  420 |
| caatgactac | agcccggggg | aggcaagcac | acagaccatc | aatcttgacg | accggtcgca  480 |
| ctggggcggc | gacctgaaaa | ccatcctgca | taccaacatg | ccaaatgtga | acgagttcat  540 |
| gtataccaat | aagtttaagg | cgcggtgat | ggtgtcgcgc | ttgcctacta | aggacaatca  600 |
| ggtggagctg | aaatacgagt | gggtggggtt | cacgctgccc | gagggcaact | actccgagac  660 |
| catgaccata | gaccttatga | acaacgcgat | cgtggagcac | tacttgaaag | tgggcagaca  720 |
| gaacggggtt | ctggaaagcg | acatcggggt | aaagtttgac | acccgcaact | tcagactgng  780 |
| gtttgacccc | gtcactggtc | ttgtcatgcc | tgggtatat | acaaacgaag | ccttccatcc  840 |
| agacatcatt | ttgctgccag | gatgnggggt | ggncttcacc | cacagccgcc | ngagcaactt  900 |
| gttgggcatc | cgcaagcngc | aaccnttcta | ggagggcttt | angatcacct | acnatgatct  960 |
| ggagggn | | | | |        967 |

<210> SEQ ID NO 8
<211> LENGTH: 84
<212> TYPE: PRT
<213> ORGANISM: Homo sapiens

<400> SEQUENCE: 8

```
Met Arg Arg Ala Ala Met Tyr Glu Glu Gly Pro Pro Tyr Tyr Glu
1               5                   10                  15

Ser Val Val Ser Ala Ala Pro Val Ala Ala Ala Leu Gly Ser Thr Phe
            20                  25                  30

Asp Ala Pro Leu Asp Pro Pro Phe Val Pro Pro Arg Tyr Leu Arg Pro
        35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr
```

<210> SEQ ID NO 9
<211> LENGTH: 968
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (919)..(919)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t

<400> SEQUENCE: 9

```
tttaagaagg aganatacat atgcggggtt ctcatcatca tcatcatcat ggtatggcta    60
gcatgactgg tggacagcaa atgggtcggg atctgtacga cgatgacgat aaggatcgat   120
ggggatccat gcggcgcgcg gcgatgtatg aggaaggtcc tcctccctcc tacgagagtg   180
tggtgagcgc ggcgccagtg gcggcggcgc tgggttctcc cttcgatgct ccctggacc    240 cgccgtttgt gcctccgcgg tacctgcggc ctaccggggg gagaaacagc atccgttact   300
ctgagttggc ccctattc gacaccaccc gtgtgtacct ggtggacaac aagtcaacgg    360
atgtggcatc cctgaactac cagaacgacc acagcaactt tctgaccacg gtcattcaaa   420
acaatgacta cagcccgggg gaggcaagca cacagaccat caatcttgac gaccggtcgc   480
actggggcgg cgacctgaaa accatcctgc ataccaacat gccaaatgtg aacgagttca   540 tgttaccaa taagtttaag gcgcgggtga tggtgtcgcg cttgcctact aaggacaatc   600
aggtggagct gaaatacgag taggtggagt tcacgctgcc cgagggcaac tactccgaga   660
ccatgaccat agaccttatg aacaacgcga tcgtggagca ctacttgaaa gtgggcagac   720
agaacggggt tctggaaagc gacatcgggg taaagtttga cacccgcaac ttcagactgg   780 ggttttgaccc cgtcactggt cttgtcatgc ctggggtata tacaaacgaa gccttccatc   840
cagacatcat tttgctgcca ggatgcgggg tggncttcac ccacagccgc ctgagcaact   900
tgttgggcat ccncaagcng caaccncttc caggagggct ttaggatcac ctacgatgat   960
``` ctggaggg 968

```
<210> SEQ ID NO 10
<211> LENGTH: 164
<212> TYPE: PRT
<213> ORGANISM: Homo sapiens

<400> SEQUENCE: 10
```

Met Arg Arg Ala Ala Met Tyr Glu Glu Gly Pro Pro Ser Tyr Glu
1               5                   10                  15

Ser Val Val Ser Ala Ala Pro Val Ala Ala Leu Gly Ser Pro Phe
                20                  25                  30

Asp Ala Pro Leu Asp Pro Pro Phe Val Pro Arg Tyr Leu Arg Pro
                35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
                100                 105                 110

Leu Asp Asp Arg Ser His Trp Gly Gly Asp Leu Lys Thr Ile Leu His
            115                 120                 125

Thr Asn Met Pro Asn Val Asn Glu Phe Met Phe Thr Asn Lys Phe Lys
    130                 135                 140

Ala Arg Val Met Val Ser Arg Leu Pro Thr Lys Asp Asn Gln Val Glu
145                 150                 155                 160

Leu Lys Tyr Glu

```
<210> SEQ ID NO 11
<211> LENGTH: 1097
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (929)..(929)
<223> OTHER INFORMATION: n is a, c, g, or t
<220> FEATURE:
<221> NAME/KEY: misc_feature
<222> LOCATION: (946)..(946)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (973)..(973)
<223> OTHER INFORMATION: n is a, c, g, or t
```

```
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (985)..(985)
<223> OTHER INFORMATION: n is a, c, g, or t

<400> SEQUENCE: 11
tttaagaagg aganatacat atgcggggtt ctcatcatca tcatcatcat ggtatggcta      60
gcatgactgg tggacagcaa atgggtcggg atctgtacga cgatgacgat aaggatcgat     120
ggggatccat gcggcgcgcg gcgatgtatg aggaaggtcc tcctccctcc tacgagagtg     180
tggtgagcgc ggcgccagtg gcggcggcgc tgggttctcc cttcgatgct cccctggacc     240
cgccgtttgt gcctccgcga tacctgcggc ctaccggggg gagaaacagc atccgttact     300
ctgagttggc accctattc gacaccaccc gtgtgtacct ggtggactac aagtcaacgg      360
atgtggcatc cctgaactac cagaacgacc acagcaactt tctgaccacg gtcattcaaa     420
acaatgacta cagcccgggg gaggcaagca cacagaccat caatcttgac gaccggtcgc     480
actggggcgg cgacctgaaa accatcctgc ataccaacat gccaaatgtg aacgagttca     540
tgtttaccaa taagtttaag gcgcgggtga tggtgtcgcg cttgcctact aaggacaatc     600
aggtggagct gaaatacgag tgggtggagt tcacgatgcc cgagggcaac tactccgaga     660
ccatgaccat agaccttatg aacaacgcga tcgtggagca ctacttgaaa gtgggcagac     720
agaacggggt tctggaaagc gacatcgggg taaagtttga cacccgcaac ttcagactgg     780
ggtttgaccc cgtcactggt cttgtcatgc ctggggtata tacaaacgaa gccntccatc     840
cagacatcat tttgctgcca ggatgcgggg tgnacttcac ccacagccgc ctgagcaact     900
tgttgggcat ccgcaagcgg caacccntnc caggagggct ttaggntcac ctacgatgat     960
ctggagggnt ggnancattc ccgcnctgtc tgccaggatg cggggtggac ttcacccaca    1020
gccgcctgag caacttgttg ggcatccgca agcggcaacc cttccaggag ggctttagga    1080
tcacctacga tgatctg                                                   1097

<210> SEQ ID NO 12
<211> LENGTH: 271
<212> TYPE: PRT
<213> ORGANISM: Homo sapiens
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid

<400> SEQUENCE: 12

Met Arg Arg Ala Ala Met Tyr Glu Glu Gly Pro Pro Pro Ser Tyr Glu
1               5                   10                  15

Ser Val Val Ser Ala Ala Pro Val Ala Ala Ala Leu Gly Ser Pro Phe
                20                  25                  30

Asp Ala Pro Leu Asp Pro Pro Phe Val Pro Pro Arg Tyr Leu Arg Pro
            35                  40                  45

Thr Gly Gly Arg Asn Ser Ile Arg Tyr Ser Glu Leu Ala Pro Leu Phe
```

```
                    50                  55                  60
Asp Thr Thr Arg Val Tyr Leu Val Asp Tyr Lys Ser Thr Asp Val Ala
 65                  70                  75                  80

Ser Leu Asn Tyr Gln Asn Asp His Ser Asn Phe Leu Thr Thr Val Ile
                 85                  90                  95

Gln Asn Asn Asp Tyr Ser Pro Gly Glu Ala Ser Thr Gln Thr Ile Asn
            100                 105                 110

Leu Asp Asp Arg Ser His Trp Gly Gly Asp Leu Lys Thr Ile Leu His
        115                 120                 125

Thr Asn Met Pro Asn Val Asn Glu Phe Met Phe Thr Asn Lys Phe Lys
    130                 135                 140

Ala Arg Val Met Val Ser Arg Leu Pro Thr Lys Asp Asn Gln Val Glu
145                 150                 155                 160

Leu Lys Tyr Glu Trp Val Glu Phe Thr Met Pro Glu Gly Asn Tyr Ser
                165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
        195                 200                 205

Lys Phe Asp Thr Arg Asn Phe Arg Leu Gly Phe Asp Pro Val Thr Gly
    210                 215                 220

Leu Val Met Pro Gly Val Tyr Thr Asn Glu Ala Xaa His Pro Asp Ile
225                 230                 235                 240

Ile Leu Leu Pro Gly Cys Gly Val Xaa Phe Thr His Ser Arg Leu Ser
                245                 250                 255

Asn Leu Leu Gly Ile Arg Lys Arg Gln Pro Xaa Pro Gly Gly Leu
            260                 265                 270

<210> SEQ ID NO 13
<211> LENGTH: 965
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (928)..(928)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (950)..(950)
<223> OTHER INFORMATION: n is a, c, g, or t
<220> FEATURE:
```

<221> NAME/KEY: misc_feature
<222> LOCATION: (962)..(962)
<223> OTHER INFORMATION: n is a, c, g, or t

<400> SEQUENCE: 13

```
tttaagaagg aganatacat atgcggggtt ctcatcatca tcatcatcat ggtatggcta      60
gcatgactgg tggacagcaa atgggtcggg atctgtacga cgatgacgat aaggatcgat     120
ggggatccat gcggcgcgcg gcgatgtatg aggaaggtcc tcctccctcc tacgagagtg     180
tggtgagcgc ggcgccagtg gcggcggcgc tgggttctcc cttcgatgct cccctggacc     240
cgccgtttgt gcctccgcgg tacctgcggc ctaccggggg gagaaacagc atccgttact     300
ctgagttggc acccctattc gacaccaccc gtgtgtacct ggtggacaac aagtcaacgg     360
tgtggcatcc ctgaactacc agaacgacca cagcaacttt ctgaccacgg tcattcaaaa     420
cagtgactac agcccggggg aggcaagcac acagaccatc aatcttgacg accggtcgca     480
ctggggcggc gacctgaaaa ccatcctgca taccaacatg ccaaatgtga acgagttcat     540
gtttaccaat aagtttaagg cgcgggtgat ggtgtcgcgc ttgcctacta aggacaatca     600
ggtggagctg aaatacgagt gggtggagtt cacgctgccc gagggcaact actccgagac     660
catgaccata gaccttatga caacgcgat cgtggagcac tacttgaaag tgggcagaca     720
gaacgggggtt ctggaatgcg acatcggggt aaagtttgac acccgcaact tcagactggg     780
gtttgatccc gtcactggtc ttgtcatgnc tggggtatat acaaacgaag ccttccatcc     840
agacatcatt tgctgccag gatgcggggt ggacttcacc cacagccgcc tgagcaactt     900
gntgggcatc cgcatgcggc aancnttncn ggagggcttt aggatcaccn acgatgatct     960
gnagg                                                                  965
```

<210> SEQ ID NO 14
<211> LENGTH: 83
<212> TYPE: PRT
<213> ORGANISM: Homo sapiens

<400> SEQUENCE: 14

```
Gly Ser Met Arg Arg Ala Ala Met Tyr Glu Glu Gly Pro Pro Pro Ser
1               5                   10                  15

Tyr Glu Ser Val Val Ser Ala Ala Pro Val Ala Ala Leu Gly Ser
            20                  25                  30

Pro Phe Asp Ala Pro Leu Asp Pro Phe Val Pro Pro Arg Tyr Leu
        35                  40                  45

Arg Pro Thr Gly Gly Arg Asn Ser Ile Arg Tyr Ser Glu Leu Ala Pro
    50                  55                  60

Leu Phe Asp Thr Thr Arg Val Tyr Leu Val Asp Asn Lys Ser Thr Val
65                  70                  75                  80

Trp His Pro
```

<210> SEQ ID NO 15
<211> LENGTH: 999
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:

<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (972)..(973)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (977)..(977)
<223> OTHER INFORMATION: n is a, c, g, or t
<220> FEATURE:
<221> NAME/KEY: misc_feature
<222> LOCATION: (982)..(982)
<223> OTHER INFORMATION: n is a, c, g, or t
<220> FEATURE:
<221> NAME/KEY: misc_feature
<222> LOCATION: (992)..(992)
<223> OTHER INFORMATION: n is a, c, g, or t
<220> FEATURE:
<221> NAME/KEY: misc_feature
<222> LOCATION: (997)..(997)
<223> OTHER INFORMATION: n is a, c, g, or t

<400> SEQUENCE: 15

```
tttactttaa gaaggagana tacatatgcg gggttctcat catcatcatn atcatggtat    60
ggctagcatg actggtggac agcaaatggg tcgggatctg tacgacgatg acgataagga   120
tcgatgggga tccatgcggc gcgcggcgat gtatgaggaa ggtcctcctc cctcctacga   180
gagtgtggtg agcgcggcgc cagtggcggc ggcgctgggt tctcccttcg atgctcccct   240
ggacccgccg tttgtgcctc cgcggtacct gcggcctacc ggggggagaa acagcatccg   300
ttactctgag ttggcacccc tattcgacac caccgtgtg  tacctggtgg acaacaagtc   360
aacggtgtgg catccctgaa ctaccagaac gaccacagca actttctgac cacggtcatt   420
caaaacagtg actacagccc gggggaggca agcacacaga ccatcaatct tgacgaccgg   480
tcgcactggg gcggcgacct gaaaaccatc ctgcatacca acatgccaaa tgtgaacgag   540
ttcatgttta ccaataagtt taaggcgcgg gtgatggtgt cgcgcttgcc tactaaggac   600
aatcaggtgg agctgaaata cgagtgggtg gagttcacgc tgcccgaggg caactactcc   660
gagaccatga cctagacct  tatgaacaac gcgatcgtgg agcactactt gaaagtgggc   720
agacagaacg gggttctgga atgcgacatc ggggtaaagt ttgacacccg caacttcaga   780
ctggggtttg atcccgtcac tggtcttgtc atgcctgggg tatatacaaa cgaagccttc   840
catccagaca tcattttgct gccaggatgc ggggtggact caccacag  ccgcctgagc   900
aacttgttgg gcatccgcat gcggcaaccc ttncaggagg gctttaggat cacctacgat   960
gatctgnagg gnngnancat tncccgcact gntggangt                          999
```

<210> SEQ ID NO 16
<211> LENGTH: 81
<212> TYPE: PRT
<213> ORGANISM: Homo sapiens

<400> SEQUENCE: 16

```
Met Arg Arg Ala Ala Met Tyr Glu Glu Gly Pro Pro Ser Tyr Glu
1               5                   10                  15
```

Ser Val Val Ser Ala Ala Pro Val Ala Ala Leu Gly Ser Pro Phe
            20                  25                  30

Asp Ala Pro Leu Asp Pro Pro Phe Val Pro Arg Tyr Leu Arg Pro
        35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Val Trp His
65                  70                  75                  80

Pro

<210> SEQ ID NO 17
<211> LENGTH: 944
<212> TYPE: DNA
<213> ORGANISM: Homo sapiens
<220> FEATURE:
<221> NAME/KEY: misc_feature
<222> LOCATION: (846)..(847)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (940)..(940)
<223> OTHER INFORMATION: n is a, c, g, or t

<400> SEQUENCE: 17
attttgttta ctttaagaag gagatataca tatgcggggt tctcatcatc atcatcatca    60
tggtatggct agcatgactg gtggacagca aatgggtcgg gatctgtacg acgatgacga   120
taaggatcga tggggatcca tgcggcgcgc ggcgatgtat gaggaaggtc ctcctccctc   180
ctacgagagt gtggtgagcg cggcgccagt ggcggcggcg ctgggttctc ccttcgatgc   240
tccctggac ccgccgtttg tgcctccgcg gtacctgcgg cctaccgggg ggagaaacag   300
catccgttac tctgagttgg caccccctatt cgacaccacc cgtgtgtacc tggtggacaa   360
caagtcaacg gatgtggcat ccctgaacta ccagaacgac cacagcaact ttctgaccac   420
ggtcattcaa acaatgact acagcccggg ggaggcaagc acacagacca tcaatcttga   480
cgaccggtcg cactggggcg cgacctgaa aaccatcctg cataccaaca tgccaaatgt   540
gaacgagttc atgtttacca ataagtttaa ggcgcgggtg atggtgtcgc gcttgcctac   600
taaggacaat caggtggagc tgaaatacga gtaggtggag ttcacgctgc ccgagggcaa   660
ctactccgag accatgacca tagacctatt gaacaacgcg atcgtggagc tactacttgaa   720
agtgggcaga cagaacgggg ttctggaaag cgacatcggg gtaaagtttg acacccgcaa   780
cttcagactg gggttttgacc ccgtcactgg tcttgtcatg cctggggtat atacaaacga   840
agcctnncat ccagacatca ttttgctgcc aggatgcggg gtggacttca cccacagccg   900
cctgagcaac ttgttgggca tccncaagcg gcaaccctn cagg                    944

<210> SEQ ID NO 18
<211> LENGTH: 164
<212> TYPE: PRT
<213> ORGANISM: Homo sapiens

<400> SEQUENCE: 18

Met Arg Arg Ala Ala Met Tyr Glu Glu Gly Pro Pro Ser Tyr Glu
1               5                   10                  15

Ser Val Val Ser Ala Ala Pro Val Ala Ala Ala Leu Gly Ser Pro Phe
            20                  25                  30

```
Asp Ala Pro Leu Asp Pro Pro Phe Val Pro Pro Arg Tyr Leu Arg Pro
            35                  40                  45

Thr Gly Gly Arg Asn Ser Ile Arg Tyr Ser Glu Leu Ala Pro Leu Phe
 50                  55                  60

Asp Thr Thr Arg Val Tyr Leu Val Asp Asn Lys Ser Thr Asp Val Ala
 65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
               100                 105                 110

Leu Asp Asp Arg Ser His Trp Gly Gly Asp Leu Lys Thr Ile Leu His
               115                 120                 125

Thr Asn Met Pro Asn Val Asn Glu Phe Met Phe Thr Asn Lys Phe Lys
               130                 135                 140

Ala Arg Val Met Val Ser Arg Leu Pro Thr Lys Asp Asn Gln Val Glu
145                 150                 155                 160

Leu Lys Tyr Glu

<210> SEQ ID NO 19
<211> LENGTH: 1888
<212> TYPE: DNA
<213> ORGANISM: Homo sapiens
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (1870)..(1870)
<223> OTHER INFORMATION: n is a, c, g, or t
<220> FEATURE:
<221> NAME/KEY: misc_feature
<222> LOCATION: (1875)..(1875)
<223> OTHER INFORMATION: n is a, c, g, or t

<400> SEQUENCE: 19
atgcggggtt ctcatcatca tcatcatcat ggtatggcta gcatgactgg tggacagcaa      60
atgggtcggg atctgtacga cgatgacgat aaggatcgat ggggatccat gcggcgcgcg     120
gcgatgtatg aggaaggtcc tcctccctcc tacgagagtg tggtgagcgc ggcgccagtg     180
gcggcggcgc tggttctccc ttcgatgct cccctggacc accgtttgt gcctccgcgg      240 tacctgcggc ctaccggggg gagaaacagc atccgttact ctgagttggc acccctattc     300
gacaccaccc gtgtgtacct ggtggacaac aagtcaacgg atgtggcatc cctgaactac     360
cagaacgacc acagcaactt tctgaccacg tcattcaaa acaatgacta cagcccgggg      420
gaggcaagca cacagaccat caatcttgac gaccggtcgc actggggcgg cgacctgaaa     480
accatcctgc ataccaacat gccaaatgtg aacgagttca tgtttaccaa taagtttaag     540
gcgcgggtga tggtgtcgcg cttgcctact aaggacaatc aggtggagct gaaatacgag     600
tgggtggagt naccgctgcc cgagggcaac tactccgaga ccatgaccat agaccttatg     660
aacaacgcga tcgtggagca ctacttgaaa gtgggcagac agaacggggt tctggaaagc     720
gacatcgggg taaagtttga cacccgcaac ttcagactgg ggtttgaccc cgtcactggt     780
cttgtcatgc ctggggtata tacaaacgaa gccttccatc cagacatcat tttgctgcca     840
```

-continued

```
ggatgcgggg tggacttcac ccacagccgc ctgagcaact tgttgggcat ccgcaagcgg    900
caacccttcc aggagggctt taggatcacc tacgatgatc tggagggtgg taacattccc    960
gcactgttgg atgtggacgc ntaccaggcg agcttgaaag atgacaccga acagggcggg   1020
ggtggcgcag gcggcagcaa cagcagtggc agcggcgcgg aagagaactc caacgcggca   1080
gccgcggcaa tgcagccggt ggaggacatg aacgatcatg ccattcgcgg cgacaccttt   1140
gccacacggg ctgaggagaa gcgcgctgag gccgaagcag cggccgaagc tgccgccccc   1200
gctgcgcaac ccgaggtcga aagcctcag gagaaaccgg tgatcaaacc cctgacagag    1260
gacagcaaga aacgcagtta caacctaata gcaatgaca gcaccttcac ccagtaccgc    1320
agctggtacc ttgcatacaa ctacggcgac cctcagaccg aatccgctc atggaccctg    1380
ctttgcactc ctgacgtaac ctgcggctcg gagcaggtct actggtcgtt gccagacatg   1440
atgcaagacc ccatgacctt ccgctccacg cgccagatca gcaactttcc ggtggttggc   1500
gccgagctgt tgtccgtgca ctccaagagc ttctacaacg accaggccgt ctactcccaa   1560
ctcatccgcc agtttacctc tctgacccac gtgttcaatc gctttcccga aaccagatt    1620
ttggcgcgcc cgccagcccc caccatcacc accgtcagtg aaaacgttcc tgctctcaca   1680
gatcacggga cgctaccgct cgcaacagc atcggaggag tccagcgagt gaccattact    1740
gacgccagac gccgcacctg cccctacgtt tacaaggccc tgggcatagt ctcgccgcgc   1800
gtcctatcga gccgcacttt ttgagaattc gaagcttgat ccggctgcta acaaagcccg   1860
aaaggaagcn gagtnggctg ctgccacc                                       1888
```

<210> SEQ ID NO 20
<211> LENGTH: 571
<212> TYPE: PRT
<213> ORGANISM: Homo sapiens
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid

<400> SEQUENCE: 20

```
Met Arg Arg Ala Ala Met Tyr Glu Glu Gly Pro Pro Ser Tyr Glu
1               5                   10                  15

Ser Val Ser Ala Ala Pro Val Ala Ala Leu Gly Ser Pro Phe
            20                  25                  30

Asp Ala Pro Leu Asp Pro Pro Phe Val Pro Pro Arg Tyr Leu Arg Pro
        35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
            100                 105                 110

Leu Asp Asp Arg Ser His Trp Gly Gly Asp Leu Lys Thr Ile Leu His
        115                 120                 125

Thr Asn Met Pro Asn Val Asn Glu Phe Met Phe Thr Asn Lys Phe Lys
    130                 135                 140
```

```
Ala Arg Val Met Val Ser Arg Leu Pro Thr Lys Asp Asn Gln Val Glu
145                 150                 155                 160

Leu Lys Tyr Glu Trp Val Glu Xaa Thr Leu Pro Glu Gly Asn Tyr Ser
                165                 170                 175

Glu Thr Met Thr Ile Asp Leu Met Asn Asn Ala Ile Val Glu His Tyr
            180                 185                 190

Leu Lys Val Gly Arg Gln Asn Gly Val Leu Glu Ser Asp Ile Gly Val
        195                 200                 205

Lys Phe Asp Thr Arg Asn Phe Arg Leu Gly Phe Asp Pro Val Thr Gly
    210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
            260                 265                 270

Ile Thr Tyr Asp Asp Leu Glu Gly Gly Asn Ile Pro Ala Leu Leu Asp
        275                 280                 285

Val Asp Xaa Tyr Gln Ala Ser Leu Lys Asp Asp Thr Glu Gln Gly Gly
    290                 295                 300

Gly Gly Ala Gly Gly Ser Asn Ser Ser Gly Ser Gly Ala Glu Glu Asn
305                 310                 315                 320

Ser Asn Ala Ala Ala Ala Met Gln Pro Val Glu Asp Met Asn Asp
                325                 330                 335

His Ala Ile Arg Gly Asp Thr Phe Ala Thr Arg Ala Glu Glu Lys Arg
            340                 345                 350

Ala Glu Ala Glu Ala Ala Glu Ala Ala Pro Ala Ala Gln Pro
                355                 360                 365

Glu Val Glu Lys Pro Gln Glu Lys Pro Val Ile Lys Pro Leu Thr Glu
        370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
                405                 410                 415

Thr Gly Ile Arg Ser Trp Thr Leu Leu Cys Thr Pro Asp Val Thr Cys
            420                 425                 430

Gly Ser Glu Gln Val Tyr Trp Ser Leu Pro Asp Met Met Gln Asp Pro
        435                 440                 445

Met Thr Phe Arg Ser Thr Arg Gln Ile Ser Asn Phe Pro Val Val Gly
    450                 455                 460

Ala Glu Leu Leu Ser Val His Ser Lys Ser Phe Tyr Asn Asp Gln Ala
465                 470                 475                 480

Val Tyr Ser Gln Leu Ile Arg Gln Phe Thr Ser Leu Thr His Val Phe
                485                 490                 495

Asn Arg Phe Pro Glu Asn Gln Ile Leu Ala Arg Pro Ala Pro Thr
            500                 505                 510

Ile Thr Thr Val Ser Glu Asn Val Pro Ala Leu Thr Asp His Gly Thr
        515                 520                 525

Leu Pro Leu Arg Asn Ser Ile Gly Gly Val Gln Arg Val Thr Ile Thr
530                 535                 540
```

```
Asp Ala Arg Arg Arg Thr Cys Pro Tyr Val Tyr Lys Ala Leu Gly Ile
545                 550                 555                 560

Val Ser Pro Arg Val Leu Ser Ser Arg Thr Phe
                565                 570
```

ISOLATING TRAFFIC-ENHANCING MUTANTS OF DRUG DELIVERY PROTEIN

CROSS REFERENCE TO RELATED APPLICATIONS

This application is a continuation of U.S. patent application Ser. No. 14/419,233, filed on Feb. 2, 2015, which is the U.S. national phase application under 35 U.S.C. § 371 of International Application No. PCT/US2013/053493, filed on Aug. 2, 2013, which claims priority benefit of U.S. Provisional Application No. 61/679,306, filed on Aug. 3, 2012, the contents of each of which are incorporated herein by reference in their entirety.

GOVERNMENT RIGHTS

The invention was made with government support under Grant Nos. CA129822 and CA140995 awarded by the National Institutes of Health. The government has certain rights in the invention.

SUBMISSION OF SEQUENCE LISTING ON ASCII TEXT FILE

The content of the following submission on ASCII text file is incorporated herein by reference in its entirely: a computer readable form (CRF) of the Sequence Listing (file name: 761542000301SEQLIST.txt, date recorded: Jun. 21, 2018, size: 39 KB).

FIELD OF INVENTION

The invention provides methods and compositions for cell penetration function to improve drug delivery to specific organelles.

BACKGROUND OF THE INVENTION

Directed evolution has been used to generate pseudotyped adeno-associated virus (AAV) capsids with novel tropism, reduced non-specific delivery, and immune evasion (Kwon and Schaffer, 2008; Maheshri et al., 2006). Biopanning of phage display and whole viral libraries in vitro and in vivo with different selective pressures has generated proteins with desired properties such as improved ligand binding and uptake, immune interactions, or enzyme activities (Yuan et al., 2005). Thus, this methodology can be a powerful and more effective alternative to rational mutation for creating new protein variants with improved features. The most recently developed approach to this process employs error-prone PCR and staggered extension to create a library of variants that can be screened against different cell types to select out cell-specific targeted vectors (Zhao et al., 1998). To date, a process has not yet been developed to isolate protein variants with improved intracellular trafficking functions. This invention introduces a new procedure and new protein molecules with improved cell penetration functions for drug delivery resulting from the procedure.

SUMMARY OF THE INVENTION

Various embodiments include a method of enhancing trafficking to a cell, comprising providing a composition comprising a penton base (PB) protein with one or more mutations that enhance cellular entry and administering an effective dosage of the composition to the cell. In one embodiment, the one or more mutations is 111C and/or 333F. In another embodiment, the composition targets the cytoplasm and/or nucleus of the cell. In another embodiment, the composition further comprises a therapeutic drug. In another embodiment, the cell is a tumor cell. In another embodiment, the one or more mutations is SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and/or SEQ ID NO: 20.

Other embodiments include a method for producing a drug delivery molecule that targets an organelle. The method includes the following steps: a) obtaining a polynucleotide encoding the penton base (PB) gene and generating mutants of the polynucleotide, b) cloning the mutant polynucleotide into a phage vector and generating a phage library comprising the phage vectors, c) transforming cells with the phage library, d) fractioning the transformed cells and harvesting the organelle from the transformed cells, e) amplifying the phages from the harvested organelles, f) transforming cells with the amplified phages from the harvested organelle, g) repeating steps (d), (e), (f), and (g), h) titering the phages from the harvested organelles from each round, i) selecting the phages with the highest titer and obtaining the sequences of the mutant polynucleotide from the phage, and j) producing polypeptides encoded by the sequences, where the polypeptides are the drug delivery molecules that target organelles. In another embodiment, the organelle is selecting from the group consisting of mitochondrion, Golgi apparatus, endoplasmic reticulum, nucleus, ribosomes, plasma membrane and cytosol. In another embodiment, the cells are mammalian or non-mammalian cells. In another embodiment, the mutants are generated using any one or more of PCR-based methods, chemical mutagenesis, ultraviolet-induced mutagenesis or a combination thereof. In another embodiment, the drug delivery molecule comprises a targeting domain, an endosomolytic ligand domain and a positively charged domain.

Other embodiments include a carrier for delivering a therapeutic agent to an organelle, comprising a polypeptide encoded by one or more penton base (PB) mutations that enhance cellular entry. In another embodiment, the one or more penton base (PB) mutations include 111C and/or 333F. In another embodiment, the carrier further comprises a polylysine motif. In another embodiment, the carrier further comprises a targeting domain of heregulin. In another embodiment, the one or more PB mutations comprises a C-terminal deletion.

Other embodiments include a therapeutic agent comprising a carrier for delivering a therapeutic agent to an organelle comprising a polypeptide encoded by one or more penton base (PB) mutations that enhance cellular entry and a therapeutic drug. In another embodiment, the therapeutic drug is a chemotherapeutic agent.

Various other embodiments include a method of producing a carrier without proliferative activity, comprising a) obtaining a polynucleotide encoding the receptor binding domain of heregulin (Her) and generating mutants in the polynucleotide, b) cloning the mutant Her polynucleotides into phage vectors and generating a phage library comprising the phage vectors, c) transforming MDA-MB-435 cells with the phage library in the presence of mitotic inhibitors, d) fractioning the transformed cell and extracting the membrane fraction of the MDA-MB-435 cells, e) harvesting membrane phages from the membrane fraction, f) transforming the membrane phages into MDA-MB-435 cells in the presence of mitotic inhibitors, g) repeating steps (d), (e), and (f), h) monitoring MDA-MB-435 cell proliferation in each round and selecting the membrane phages with the lowest MDA-MB-435 cell proliferation, i) obtaining the sequences of the Her polynucleotide mutants in the selected membrane phages, and j) producing polypeptides encoded by the Her sequences and penton base gene, where the polypeptides are the carrier without proliferative activity.

Other embodiments include a carrier for delivering therapeutics to the nucleus, comprising a polypeptide encoded by mutant Her sequences. In another embodiment, the carrier further comprises a polypeptide encoding penton base (PB) protein and a polylysine motif. In another embodiment, the PB protein is a mutant penton base protein.

Other embodiments include a therapeutic agent comprising a carrier and a therapeutic drug.

BRIEF DESCRIPTION OF FIGURES

FIG. 5(A) depicts protein was precipitated from each fraction by acetone precipitation and pellets were resuspended in 40 uL desalting buffer, followed by analysis via SDS-PAGE and Western blotting. FIG. 5(B) depicts analysis of band densities using Image J show an increase of 111C in both cytosolic and nuclear fractions compared to the wild-type protein. Trafficking and Cell fractionation assay: Adherent HeLa cells growing in flasks were detached with 5 mL 1×PBS+2 mM EDTA at 37C incubation with agitation for 50 min and transferred to 15 mL conical tubes. The density of the cells were measured, and cells were distributed into separate tubes at 5×106 cells per tube. Cells were washed with 1×PBS+Ca2++Mg2+ three times to remove the EDTA, and cell pellets were resuspended in 0.7 ml Buffer A (20 mM HEPES, pH 7.4; 2 mM MgCl2; 3% BSA in DMEM). Wild-type (WT) or mutant (111C, 333F) penton base protein (450 ug) was added to separate cell aliquots and mixtures were incubated at 4C for 2 hrs with agitation to promote receptor binding, followed by incubation at 37C for 2 h with agitation to promote internalization of receptor-bound protein. Control treatments received no protein (NP). Cells were then collected and processed for subcellular fractionation using the Qproteome Cell Compartment assay kit (Qiagen).

FIG. 6(A) depicts intracellular trafficking and immunocytochemistry. Procedure followed the established protocols detailed in Gene Therapy (2006) 13, 821-836. Anti-penton base antibody (Ad5 antibody) was used at 1:500 dilution. Alexa-Fluor 488 Goat Anti-Rabbit was used at 1:400 dilution (2nd antibody). Phalloidin was used at 1:100 dilution, and DAPI used at 300 nM. Green, wild-type (WT) or mutant (111C, 333F) PB; Red, actin; Blue, nucleus. FIG. 6(B) depicts quantification of protein trafficking. Sixteen cells from each treatment represented in the left panel was selected for quantification. The counts were based on the histogram of each image in Adobe Photoshop. Bars represent green pixel counts within the 80-255 window in the green channel.

FIG. 8 depicts, in accordance with an embodiment herein, nucleic Acid and peptide sequence of mutated PB from Fraction 111 Clone A (111A).

FIG. 9 depicts, in accordance with an embodiment herein, nucleic acid and predicted amino acid sequence of mutated PB from Fraction 111 Clone C (111C).

FIG. 10 depicts, in accordance with an embodiment herein, nucleic acid and peptide sequence of mutated PB from Fraction 111 Clone G (111G).

FIG. 11 depicts, in accordance with an embodiment herein, nucleic acid and peptide sequence of mutated PB from Fraction 331 Clone E (331E).

FIG. 12 depicts, in accordance with an embodiment herein, nucleic acid and peptide sequence of mutated PB from Fraction 331 Clone I (331I).

FIG. 13 depicts, in accordance with an embodiment herein, nucleic acid and peptide sequence of mutated PB from Fraction 331 Clone J (331J).

FIG. 14 depicts, in accordance with an embodiment herein, nucleic acid and peptide sequence of mutated PB from Fraction 333 Clone A (333A).

FIG. 15 depicts, in accordance with an embodiment herein, nucleic acid and peptide sequence of mutated PB from Fraction 333 Clone D (333D).

FIG. 16 depicts, in accordance with an embodiment herein, nucleic acid and peptide sequence of mutated PB from Fraction 333 Clone E (333E).

FIG. 17 depicts, in accordance with an embodiment herein, nucleic acid and peptide sequence of mutated PB from Franction 333, clones F, G, and H (333F, 333G, 333H).

DETAILED DESCRIPTION OF THE INVENTION

Figure 1:
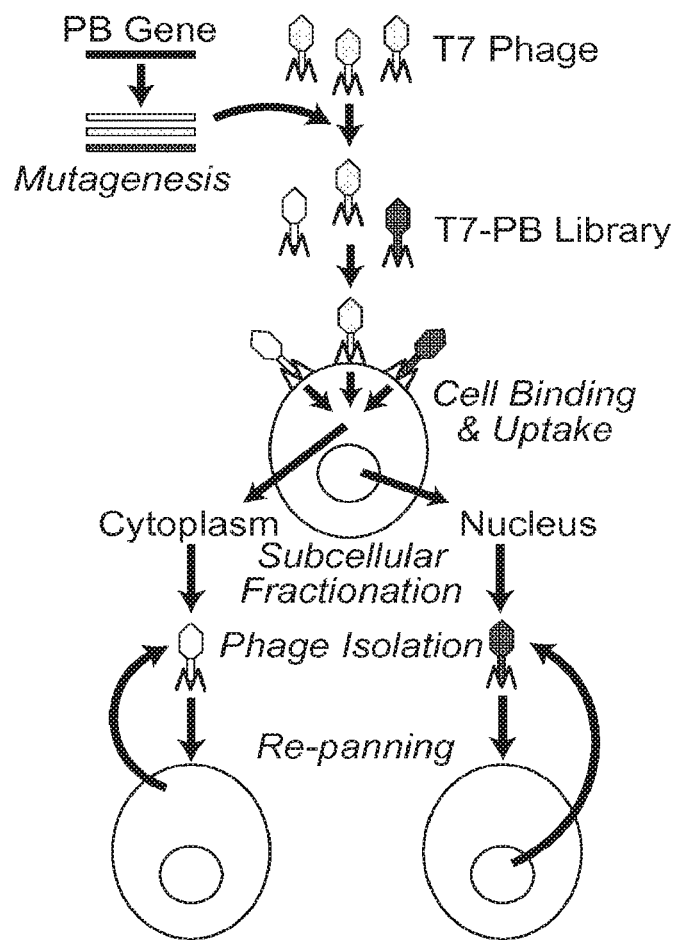
FIG. 1 depicts, in accordance with an embodiment herein, the biopanning strategy.

As used herein, the abbreviation "PB" means penton base.

A variety of reagents have been developed to deliver therapeutic genes and drugs to diseased cells, and include liposomes, synthetic polymers, peptides, proteins, viruses, and viral nanoparticles (Mcdina-Kauwc, 2006; MedinaKauwc et al., 2005). Typically, the particles formed by these reagents require modifications to facilitate delivery of gene or drug payloads. Such modifications include appending targeting ligands or antibodies, membrane penetrating agents, and/or intracellular targeting (such as nuclear targeting) agents. These modifications are usually introduced through rational design and thus each new variant generated by such modification requires empirical testing. This can be time consuming and labor intensive, and runs the risk of yielding suboptimal activity.

Past and present attempts to improve cell membrane penetration and/or intracellular trafficking have used rational design to conjugate cell penetration or intracellular targeting peptides to drug carriers. Such an approach requires empirical testing of each molecule.

Numerous types of cell penetration peptides have been tested for enhanced gene and drug delivery, and include AntP, TAT, GALA, honey bee melittin, and similar peptides (Medina-Kauwe, 2006; Medina-Kauwe et al., 2005). Likewise, nuclear targeting activity has been added to gene delivery agents via appendage of different poly-basic domains such as the SV40 NLS, HMG-1, protamine, and similar peptides or proteins (MedinaKauwe, 2006; Medina-Kauwe et al., 2005). While each of these peptides possess the capacity to penetrate cell membranes or target intracellular compartments, including the nucleus, their activities are altered when covalently coupled to another molecule or expressed as a fusion protein to another molecule. Moreover, empirical testing of each different variant of these peptides is time consuming and labor intensive. Therefore, while rational design and empirical testing is the existing solution to this problem, this approach, has its limitations.

The invention described herein circumvents the time and effort required for rational design and empirical testing of cell penetration/intracellular trafficking proteins/peptides by using selective pressure to isolate protein mutants that have acquired improved cell penetration, intracellular trafficking, and/or subcellular targeting. The protein mutants derived from this process have unique advantages over the parent proteins or existing gene/drug delivery proteins currently in use because of the improved features acquired through artificial evolution/selective pressure. Finally, the specific proteins isolated by the process described below will provide an advantage over existing cell penetrating peptides because of their improved membrane lysis and trafficking features. Therefore, they can be used to augment gene and drug delivery, and thus enhance therapeutic efficacy of particles used in nanomedicine.

The invention provides a method for producing a drug delivery molecule that targets an organelle. The method includes the steps of (a) obtaining a polynucleotide encoding the penton base gene and generating mutants of the polynucleotide; (b) cloning the mutant polynucleotide into a phage vector and generating a phage library comprising the phage vectors; (c) transforming cells with the phage library; (d) fractioning the transformed cells and harvesting the organell from the transformed cells; (e) amplifying the phages from the harvested organelles; (f) transforming cells with the amplified phages from the harvested organelle; (g) repeating steps (d), (e), (f), and (g); (h) titering the phages from the harvested organelles from each round; (i) selecting the phages with the highest titer and obtaining the sequences of the mutant polynucleotide from the phage; and (j) producing polypeptides encoded by the sequences, wherein the polypeptides are the drug delivery molecules that target organelles.

In some embodiments, the organelle is selecting from the group consisting of mitochondrion, Golgi apparatus, endoplasmic reticulum, nucleus, ribosomes, plasma membrane and cytosol. The cells may be mammalian or non-mammalian cells. Mutants may be generated using any random mutagenesis methods or targeted mutagenesis methods. Examples of methods that may be used to generate mutants include but are not limited to any one or more of PCR-based methods, chemical mutagenesis, ultraviolet-induced mutagenesis or a combination thereof. Mutations in the penton base gene may be any one or more of insertions, deletions, substitutions or a combination thereof.

In an embodiment of the invention, the drug delivery molecule comprises a targeting domain, an endosomolytic ligand domain and a positively charged domain.

The invention also provides a carrier for delivering a therapeutic agent to an organelle, comprising a polypeptide encoded by a mutant penton base gene. The mutation in the penton base gene may be isolated by a) obtaining a polynucleotide encoding the penton base gene and generating mutants of the polynucleotide; (b) cloning the mutant polynucleotide into a phage vector and generating a phage library comprising the phage vectors; (c) transforming cells with the phage library; (d) fractioning the transformed cells and harvesting the organell from the transformed cells; (c) amplifying the phages from the harvested organelles; (f) transforming cells with the amplified phages from the harvested organelle; (g) repeating steps (d), (e), (f), and (g); (h) titering the phages from the harvested organelles from each round; (i) selecting the phages with the highest titer and obtaining the sequences of the mutant polynucleotide from the phage; and (j) producing polypeptides encoded by the sequences, wherein the polypeptides are the drug delivery molecules that target organelles. The carrier further comprises a polylysine motif and a targeting domain, for example the targeting domain of heregulin.

The invention further provides a therapeutic agent comprising the carrier described above and a therapeutic drug. A therapeutic drug may be any drug that, for example, treats, inhibits, prevents, mitigates the effects of, reduce the severity of, reduce the likelihood of developing, slow the progression of and/or cure, a disease. Diseases targeted by the therapeutic agents include but are not limited to carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases. Therapeutic agents may be a chemotherapeutic agent.

The invention also provides a method of producing a carrier without proliferative activity. The method comprises (a) obtaining a polynucleotide encoding the receptor binding domain of heregulin (Her) and generating mutants in the polynucleotide; (b) cloning the mutant Her polynucleotides into phage vectors and generating a phage library comprising the phage vectors; (c) transforming MDA-MB-435 cells with the phage library in the presence of mitotic inhibitors; (for example taxol); (d) fractioning the transformed cell and extracting the membrane fraction of the MDA-MB-435 cells; (e) harvesting membrane phages from the membrane fraction; (f) transforming the membrane phages into MDA-MB-435 cells in the presence of mitotic inhibitors; (g) repeating steps (d), (e), and (f); (h) monitoring MDA-MB-435 cell proliferation in each round and selecting the membrane phages with the lowest MDA-MB-435 cell proliferation; (i) obtaining the sequences of the Her polynucleotide mutants in the selected membrane phages; and (j) producing polypeptides encoded by the Her sequences and the penton base gene, wherein the polypeptides are the carrier without proliferative activity. Mutations in the Her gene may be any one or more of insertions, deletions, substitutions or a combination thereof.

The invention further provides a carrier for delivering therapeutics to the nucleus, comprising a polypeptide encoded by the mutant Her sequences wherein the mutant Her is obtained according to the method described above. The carrier further comprises a polypeptide encoding penton base protein and a polylysine motif. The penton base protein may be a mutant protein.

EXAMPLES

Example 1

Isolation of Traffic-Enhancing Mutants.

Previously, a recombinant adenovirus penton base protein was developed to target and deliver a variety of therapeutic molecules to tumor cells in vitro and in vivo (Agadjanian et al., 2012; Agadjanian et al., 2009; Agadjanian et al., 2006; Medina-Kauwe et al., 2001a; Medina-Kauwe et al., 2001b; Rentsendorj et al., 2008). Currently, the penton base recombinant protein (the same one that comprises the 'PB' domain of HerPBK10, used to target therapeutics to HER2+ tumor cells; (Agadjanian et al., 2012; Agadjanian et al., 2009; Agadjanian et al., 2006; MedinaKauwe et al., 2001b; Rentsendorj et al., 2008) proceeds through multiple cell entry routes after cell binding, some but not all of which support membrane penetration and entry into the cytosol (Rentsendorj et al., 2006). To improve upon this function and enhance the delivery and penetration of therapeutics into cell targets, a directed evolution approach was used to isolate penton base variants with enhanced cell penetration activity by using nuclear accumulation as a readout, as endosomal escape enables entry into the nucleus (Rentsendorj et al., 2006).

Figure 2:
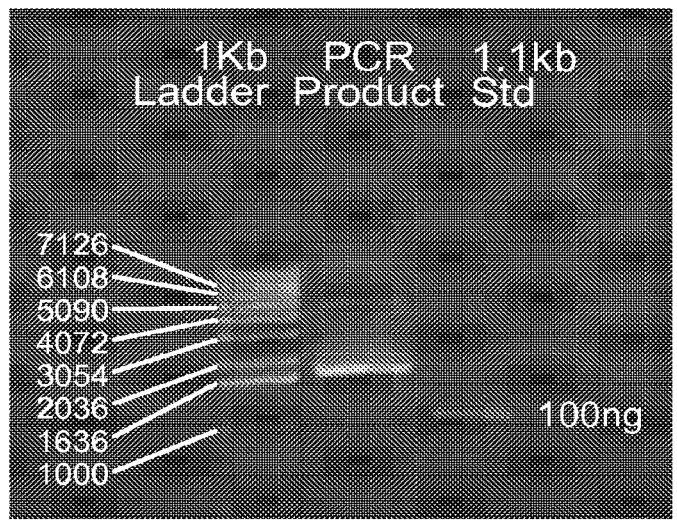
FIG. 2 depicts, in accordance with an embodiment herein, a PCR-based random mutagenesis of the penton base gene. The PCR product (just above the 1600 bp band) contains 100 ng DNA, based on densitometry analysis, giving us a total yield of ~4800 ng. As the initial target DNA was 97 ng, we have a yield/initial ratio of ~50 and a duplication number of ~5.6, which when extrapolated against the standard curve provided in the manufacturer's protocol (Genemorph II, Strategene, La Jolla, Calif., USA), corresponds to a mutation rate of ~8/kb.

Procedures:

This two-step process involves: 1. Creation of a mutant library through random mutagenesis, and 2. Introduction of a selective pressure to isolate variants with improved function, depending on the screening process. Here, isolation of phage that survive entry into the cytosol and/or nucleus will serve as the selective pressure, which is expected to yield variants with enhanced cell penetration activity (Summarized in FIG. 1). Accordingly, the inventors have randomly mutagenized the penton base gene and generated a library of mutants cloned into a K. T7 phage vector. Based on previously established directed evolution studies (Cherry et al., 1999; Shafikhani et al., 1997; Wan et al., 1998; You and Arnold, 1996), the inventors aimed for a mutation frequency of 1-4 amino acid changes (or 2-7 nucleotide changes) per gene. Based on the product yield using a specialized error-prone polymerase chain reaction (PCR) method (GeneMorphll Random Mutagenesis Kit; Stratagene, La Jolla, Calif., USA), the inventors achieved an estimated mutation frequency of ~8 nucleotides/kb or 13.6 nucleotides per penton base gene (FIG. 2). The inventors inserted this product into a T7-Select phage vector and packaged recombinant phage to produce an amplified library titer of $5 \times 10^{10}$ pfu/mL.

The library was panned onto HeLa cells (which express integrin receptors for binding and uptake of the PB protein). Phage were incubated on the cells at 4° C. for 1 h to promote receptor binding but not uptake, then cells were washed and incubated for 2 h at 37° C. to promoted internalization. After uptake, harvested cells underwent fractionation to isolate cytosolic and nuclear fractions. Phage amplified from each fraction then underwent repeated biopanning, and corresponding sequential fractions were extracted from cell harvests (i.e. nuclear phage isolated from round 1 were amplified and added back to cells, followed by repeat isolation of nuclear fractions to re-obtain nuclear phage). After either two or three rounds of biopanning, phage isolated from each repeat fraction was titered to determine the relative enrichment of nuclear/cytosolic phage from the mutagenized library compared to phage displaying wild-type penton base.

Figure 3:
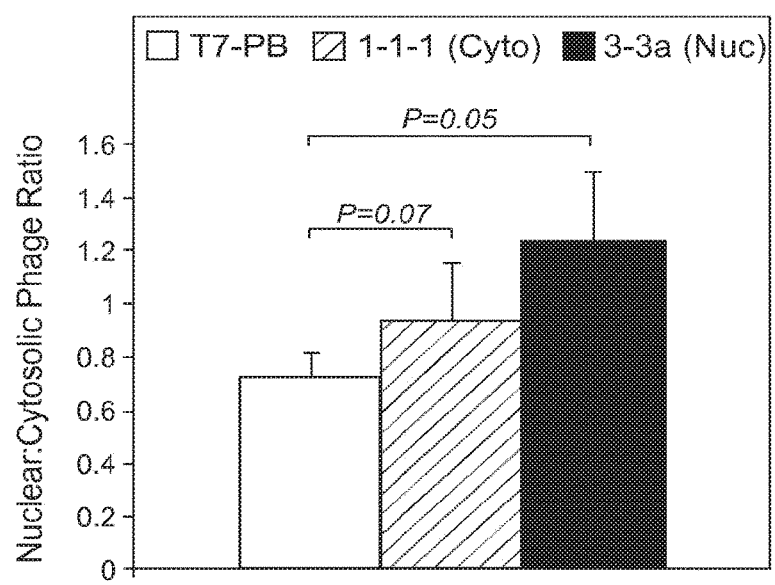
FIG. 3 depicts, in accordance with an embodiment herein, isolation of phage displaying penton base variants with enhanced partitioning in nuclear compartment. A T7 phage library displaying randomly mutagenized PB was added to 1×10^6 HeLa cells at 1×10^8 pfu following the conditions described in the text for cell binding and uptake. Cells were harvested by trypsinization to remove any surface-bound phage, then fractionated using a commercial fractionation kit (Qproteome Cell Compartment Kit; Qiagen Inc., Valencia, Calif., USA). Phage was PEG-precipitated overnight from each fraction following standard procedures, then resuspended in TB bacterial media and added to BLT5403 bacteria to amplify the isolated phage. Amplified phage was titered by plaque assay, then re-panned on HeLa using the same titer and conditions as described earlier. The phage obtained from cytosolic fractions underwent 3 rounds of cytosolic biopanning, whereas that obtained from nuclear fractions underwent 2 rounds.

Results:

The non-mutagenized parent phage, T7-PB, yielded a nuclear/cytosolic phage titer ratio of less than 1, indicating that the proportion of phage arriving at the nucleus by 2 h was less than the proportion of phage that remained in the cytoplasm (FIG. 3). In contrast, after 2 rounds of biopanning and isolation of nuclear phage (3-3a), a shift was observed toward higher nuclear accumulation compared to cytoplasmic retention, with a significant increase compared to T7-PB (P=0.05) (FIG. 3). Even phage isolated from 3 rounds of cytosolic fraction panning (1-1-1) showed a relative, though not highly significant (P=0.07), increase in nuclear partitioning compared to T7-PB (FIG. 3).

Figure 4:
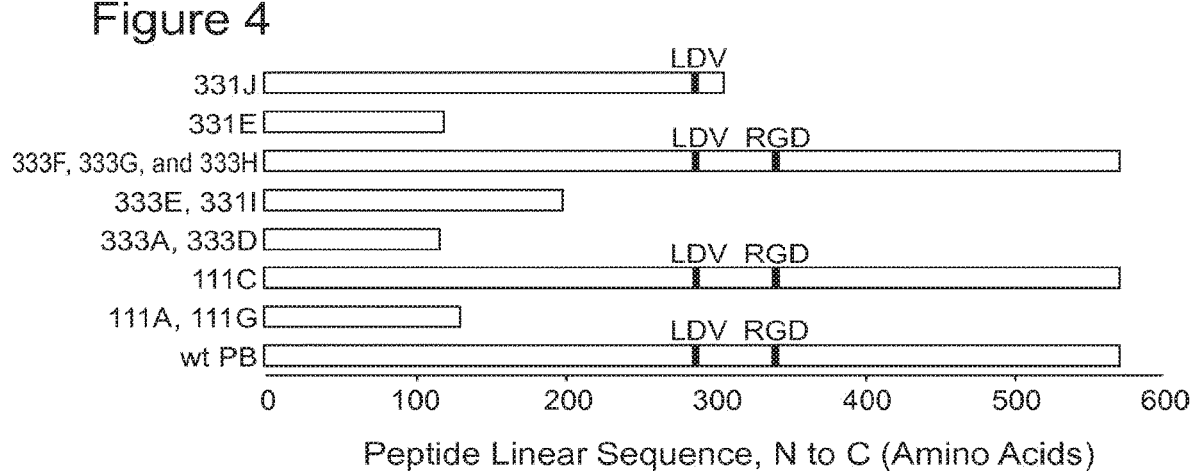
FIG. 4 depicts, in accordance with an embodiment herein, the alignment of trafficking variants isolated from biopanning.
Figure 5:
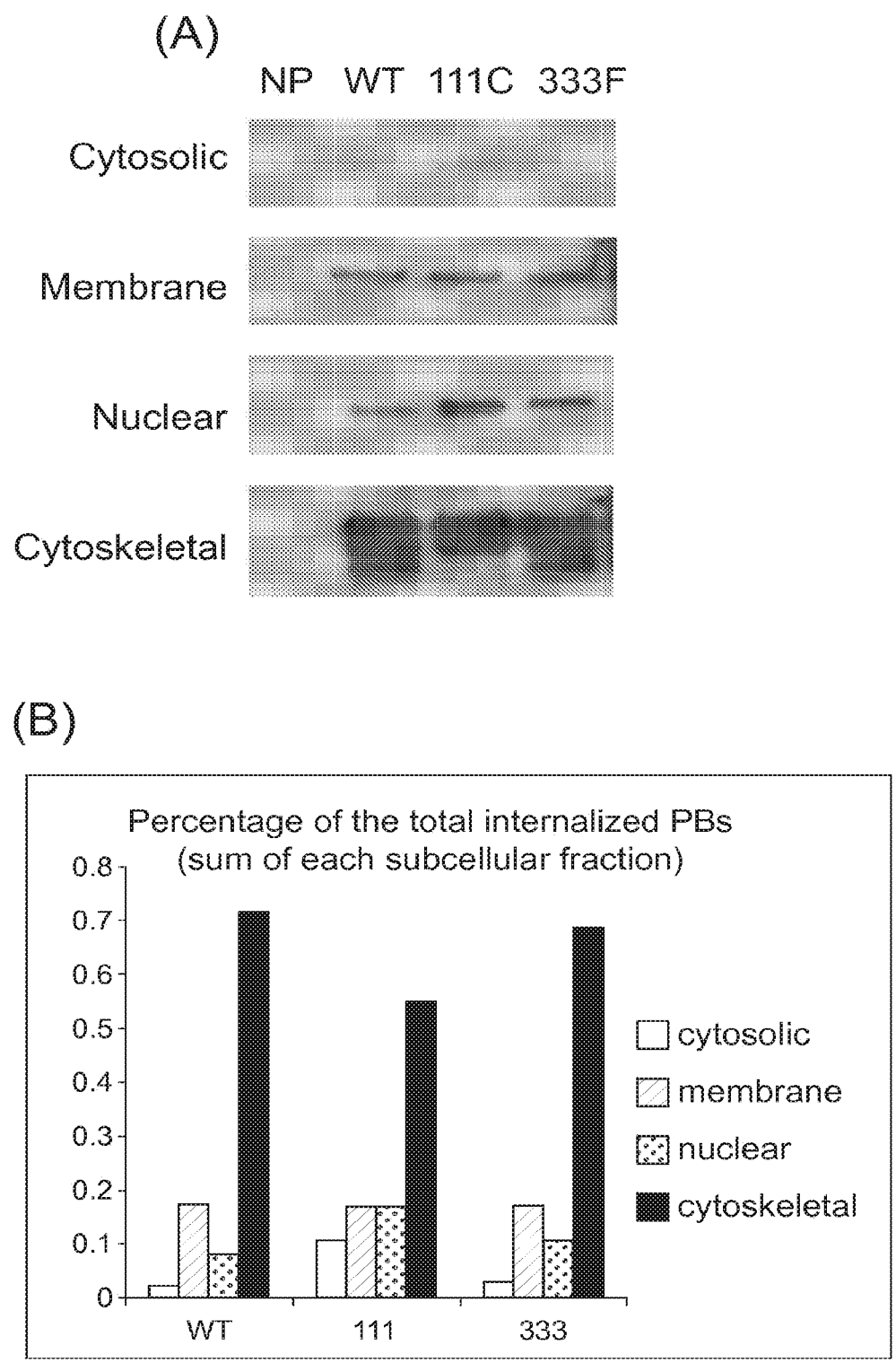
FIG. 5 depicts, in accordance with an embodiment herein, full-length mutant, 111C, exhibits enhanced trafficking to cytoplasm and nucleus.
Figure 6:
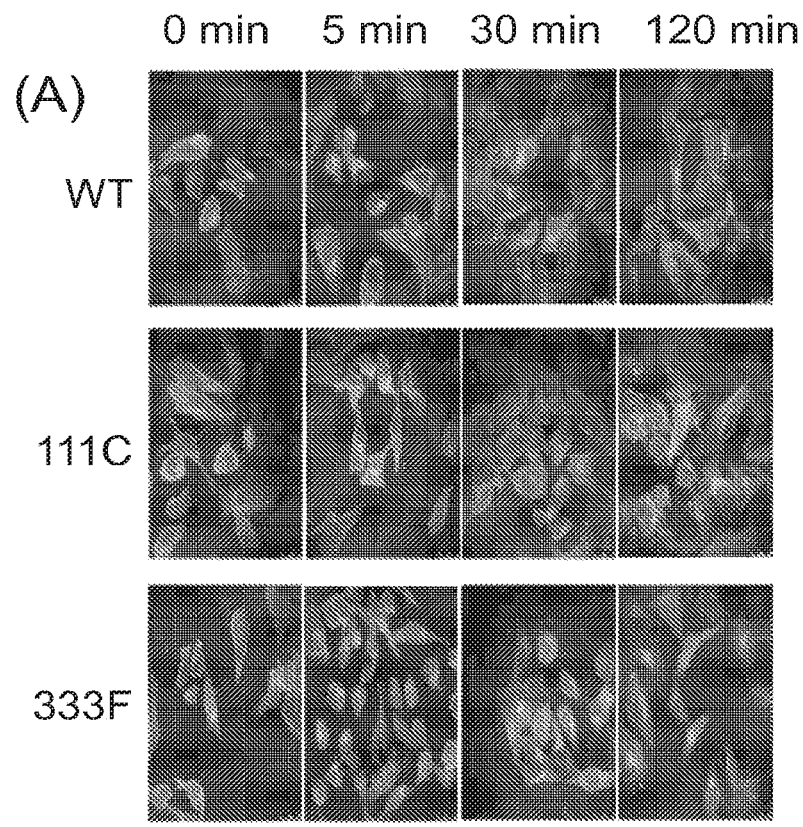
FIG. 6 depicts, in accordance with an embodiment herein, PB mutants, 111C and 333F, exhibit enhanced nuclear entry compared to wild-type PB.
Figure 6:
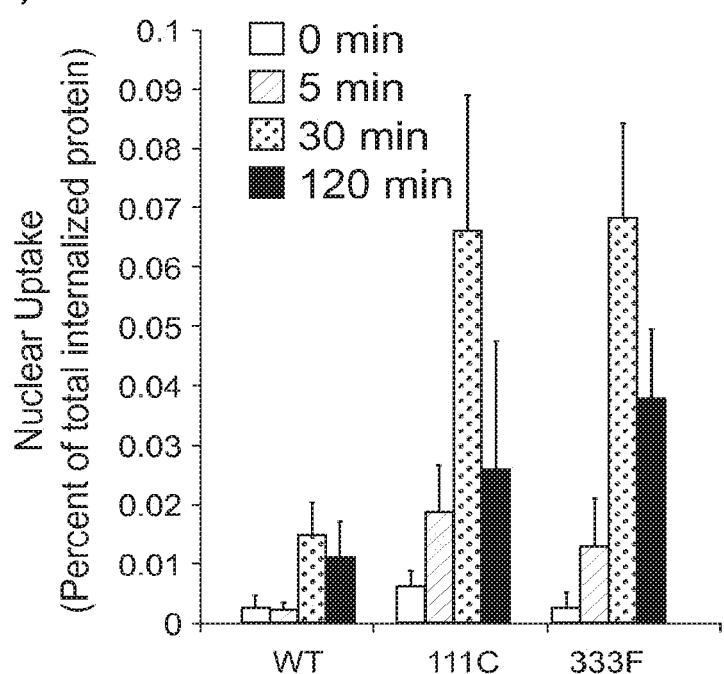
Figure 7:
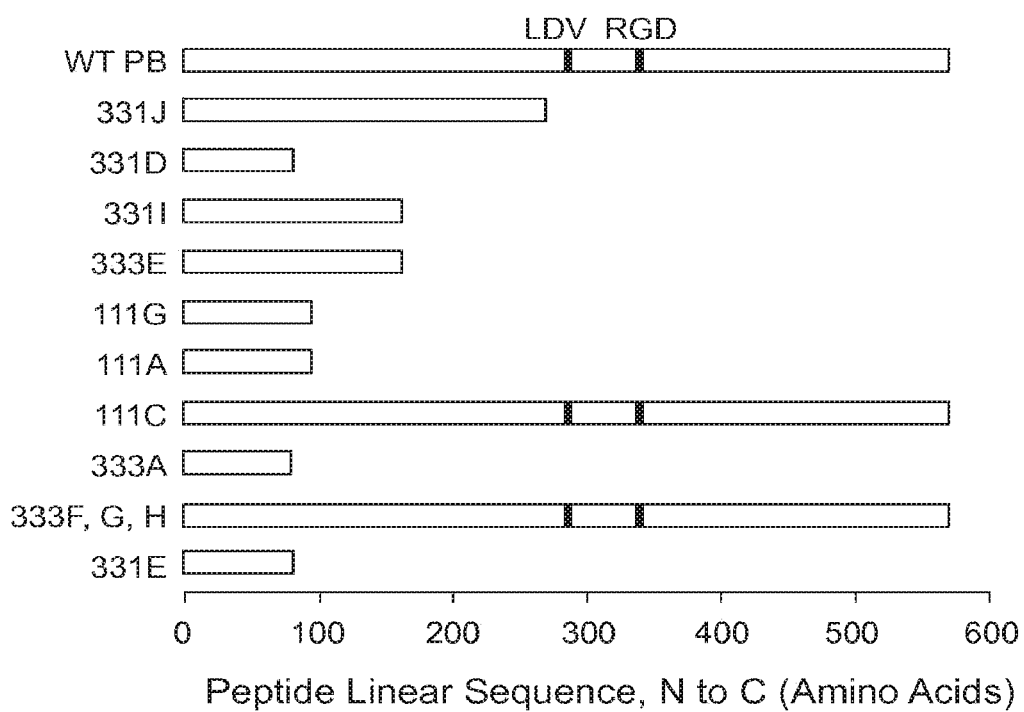
FIG. 7 depicts, in accordance with an embodiment herein, an updated Alignment of PB Mutants. New peptide lengths are based on amino acid sequences translated from nucleic acid sequences of mutant clones. Sequences are provided in FIGS. 8-17 herein.

After three rounds of biopanning and isolation of cytosolic and nuclear mutants, the inventors sequenced clones picked randomly from each enriched population and found that the majority of clones isolated from both cytosolic and nuclear fractions encoded carboxy-[C-] terminal truncated protein (FIG. 4). The 287LDV and 340RGD integrin binding motifs located near the middle of the wild-type penton base (wt PB) linear sequence were not retained in most of the truncated clones. One of the truncated mutants contains the LDV but not RGD motif, whereas the remaining truncations lack both LDV and RGD motifs. The full-length clones isolated from the biopanning retain both LDV and ROD motifs but also contain several point mutations that introduce potential function-altering amino acid changes (FIG. 4). Among these are a Leu60Trp replacement in cytosolic fraction clone 111C; and Lys375Glu, Val449Met, and Pro469Ser amino acid changes in nuclear fraction clone 333F. To test the ability of each isolated variant to impart enhanced cytosolic and/or nuclear penetration, the intracellular trafficking of each will be compared to the parent protein by immunofluorescence and confocal microscopy, and confirmed by subcellular fractionation. Specifically, as the full-length mutants (111C and 333F) and mutant 331J retain the integrin binding motifs, these variants are tested in comparison to wt PB, as they are predicted to enter cells via integrin binding and uptake. Meanwhile, as the remaining truncated variants lack any receptor-binding motifs, these will be inserted into HerPBK10 to replace the PB domain, and tested in comparison to parental HerPBK10, which enters cells via human epidermal growth factor receptor (HER) binding and uptake.

Example 2

Isolation of Receptor-Binding and Endocytosis Mutants with Blunted Signaling.

Rationale:

The tumor-targeted cell penetration protein, HerPBK10, is specifically directed to the human epidermal growth factor receptor (HER) via inclusion of the receptor binding domain of heregulin, designated here as the 'Her' domain of HerPBK10 (Medina-Kauwe et al., 2001b). However, ligation of heregulin receptors can induce signaling that may result in tumor cell proliferation, differentiation, and in some cases, apoptosis, depending on several factors including receptor heterodimer ratio, ligand subtype, cell type, and presence of certain intracellular molecules (Aguilar et al., 1999; Lewis et al., 1996; Weinstein et al., 1998). The possibility of inducing adverse effects such as tumor progression leads to examining whether the selective pressure introduced by mitotic inhibitors can select receptor binding and endocytosis mutants that lack proliferative signaling. The inventors proposed testing this approach by generating a phage library displaying Her variants and screen the library for internalizing Her species lacking proliferative signaling by isolating internalized phage from quiescent cells, and re-panning on non-proliferating human breast cancer cells.

Procedure:

A library of Her sequences containing different mutations distributed across the coding sequence will be produced by error-prone PCR and staggered extension, which entails repeated cycles of denaturation and brief annealing/extension after initial priming of template sequences (Zhao et al., 1998). The resulting library will be inserted into the appropriate vector arms for transfer into T7Select bacteriophage (which is developed to display whole proteins), and recombinant phage produced following manufacturer's instructions (Novagen, Gibbstown, N.J., USA). Based on biopanning of evolved AAV capsids, an initial titer of $10^{\wedge}12$ phage will be added to MDA-MB-435 cells maintained in media containing mitotic inhibitor such as taxol, and at about 30-45 min later (the time required for binding and internalization; Medina-Kauwe et al., 2000) the cells will be harvested by trypsin/EDTA (to remove non-internalized phage) and membrane-extracted to isolate the vesicle fraction of crude virus (Qproteome Plasma Membrane Protein Kit, Qiagen Inc., Valencia, Calif., USA), which can then be isolated by CsCl banding. Three to four rounds of selection (i.e. adding isolated virus to fresh cells and repeating membrane extraction) will be performed and isolated virus will be characterized in the following ways. First, fresh cells receiving enriched virus will be fixed and processed for immunofluorescence using an anti-phage antibody (Sigma-Aldrich, St. Louis, Mo., USA) to confirm that the isolated phage still internalize. Separate cells treated in parallel will be assessed for proliferation rate in comparison to mock and untreated cells, by metabolic assay. Second, the Her sequence from isolated phage will be excised and inserted into a bacterial expression vector for recombinant protein production (Medina-Kauwe et al., 2001a), then mutant Her tested for internalization and proliferative activity in MDA-MB-435 human breast cancer cells as described earlier, in comparison to parental Her as well as mock and untreated cells. The mutant clones will be sequenced to identify mutated regions, and inserted back into the HerPBK10 expression cassette, replacing parental 'Her'.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A carrier polypeptide, comprising a penton base polypeptide that is truncated at the C-terminus, thereby not comprising a region of the wild-type penton base polypeptide starting from an RGD motif through the C-terminus.

2. The carrier polypeptide of claim 1, further comprising a positively-charged domain.

3. The carrier polypeptide of claim 2, wherein the positively-charged domain is a polylysine motif.

4. The carrier polypeptide of claim 2, wherein the carrier polypeptide is complexed with a therapeutic drug or a gene.

5. The carrier polypeptide of claim 2, wherein the carrier polypeptide is complexed with a chemotherapeutic drug.

6. The carrier polypeptide of claim 2, wherein the penton base polypeptide comprises the penton base polypeptide sequence of SEQ ID NO: 2, SEQ ID NO: 10, residues 3-81 of SEQ ID NO: 14, SEQ ID NO: 16, or SEQ ID NO: 18.

7. The carrier polypeptide of claim 1, further comprising a cell-targeting domain.

8. The carrier polypeptide of claim 7, wherein the cell-targeting domain targets a diseased cell.

9. The carrier polypeptide of claim 7, wherein the cell-targeting domain targets a cancer cell.

10. The carrier polypeptide of claim 7, wherein the cell-targeting domain is heregulin or a mutant thereof.

11. A method of enhancing nuclear subcellular localization of a carrier polypeptide in a cell, comprising administering the carrier polypeptide to the cell, the carrier polypeptide comprising a penton base polypeptide,
wherein the penton base polypeptide is truncated at the C-terminus, thereby not comprising a region of the wild-type penton base polypeptide starting from an RGD motif through the C-terminus.

12. The method of claim 11, wherein the carrier polypeptide is complexed with a therapeutic drug or a gene.

13. The method of claim 11, wherein the cell is a tumor cell.

14. The method of claim 11, wherein the carrier polypeptide further comprises a positively-charged domain.

15. The method of claim 14, wherein the positively-charged domain is a polylysine motif.

16. The method of claim 11, wherein the carrier polypeptide further comprises a cell-targeting domain.

17. The method of claim 16, wherein the cell-targeting domain targets a diseased cell.

18. The method of claim 16, wherein the cell-targeting domain targets a cancer cell.

19. The method of claim 16, wherein the cell-targeting domain is heregulin or a mutant thereof.

20. The method of claim 11, wherein the penton base polypeptide comprises the penton base polypeptide sequence of SEQ ID NO: 2, SEQ ID NO: 10, residues 3-81 of SEQ ID NO: 14, SEQ ID NO: 16, or SEQ ID NO: 18.

* * * * *